United States Patent
Mizoshita et al.

(10) Patent No.: US 7,608,673 B2
(45) Date of Patent: Oct. 27, 2009

(54) ORGANOSILANE COMPOUND AND ORGANOSILICA OBTAIN THEREFROM

(75) Inventors: Norihiro Mizoshita, Nagoya (JP); Yasutomo Goto, Owariasahi (JP); Shinji Inagaki, Nagoya (JP); Toyoshi Shimada, Soraku-gun (JP)

(73) Assignees: Kabushiki Kaisha Toyota Chuo Kenkyusho, Aichi-Gun (JP); Toyoshi Shimada, Soraku-Gun (JP)

( * ) Notice: Subject to any disclaimer, the term of this patent is extended or adjusted under 35 U.S.C. 154(b) by 0 days.

(21) Appl. No.: 12/073,347

(22) Filed: Mar. 4, 2008

(65) Prior Publication Data

US 2008/0227941 A1 Sep. 18, 2008

(30) Foreign Application Priority Data

Mar. 7, 2007 (JP) .............................. 2007-057342

(51) Int. Cl.
*C08F 130/08* (2006.01)
(52) U.S. Cl. .................. 526/279; 556/463; 556/482
(58) Field of Classification Search .................. 526/279; 556/463, 482
See application file for complete search history.

(56) References Cited

U.S. PATENT DOCUMENTS

2008/0227939 A1 9/2008 Mizoshita et al.

FOREIGN PATENT DOCUMENTS

| JP | 2006089588 | * | 4/2006 |
| JP | A-2006-089588 | | 4/2006 |
| JP | A-2008-247886 | | 10/2008 |

OTHER PUBLICATIONS

Kapoor et al., An Alternate Route for the Synthesis of Hybrid Mesoporous Organosilica with Crystal-Like Pore Walls from Allylorganosilane Precursors, Journal of the American Chemical Society (2005), 127(22), 8174-8178.*

Deng et al.; *An Efficient Convergent Synthesis of Novel Anisotropic Adsorbates Based on Nanometer-Sized and Tripod-Shaped Oligophenylenes End-Capped with Triallylsilyl Groups; The Journal of Organic Chemistry*; vol. 67; pp. 5279-5283; 2002.

Kapoor et al.; *An Alternate Route for the Synthesis of Hybrid Mesoporous Organosilica with Crystal-Like Pore Walls from Allylorganosilane Precursors; J. Am. Chem. Soc.*; vol. 127; No. 22; pp. 8174-8178; 2005.

Kapoor et al.; *Self-assembly of cubic phenylene bridged mesoporous hubrids from allylorganosilane precursors; Journal of Materials Chemistry*; vol. 16; pp. 3305-3311; 2006.

Yoshifumi Maegawa et al., New Approach to Well-Designed Organic-Inorganic Hybrid Materials: Novel Synthesis of Allylsilylarenes with Carbon-Metal Bond (C-Mg, C-B, C-Sn) (Nara National College of Technology; CREST), The 87th Spring Meeting of the Chemical Society of Japan (2007), Mar. 25-28, 2007 at Osaka, Japan.

* cited by examiner

*Primary Examiner*—Sikarl A Witherspoon
*Assistant Examiner*—Chukwuma O Nwaonicha
(74) *Attorney, Agent, or Firm*—Oliff & Berridge, PLC

(57) ABSTRACT

Provided is an organosilane compound expressed by the following general formula (1):

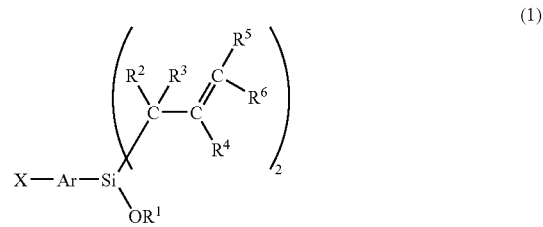

where: Ar represents a divalent aromatic organic group, such as a phenylene group; $R^1$ represents a hydrogen atom or the like; $R^2$ to $R^6$, which may be the same or different from each other, each represent a hydrogen atom or the like; and X represents a reactive substituent, such as a halogen atom.

5 Claims, 5 Drawing Sheets

WAVELENGTH (nm)

WAVELENGTH (nm)

ORGANOSILANE COMPOUND AND ORGANOSILICA OBTAIN THEREFROM

BACKGROUND OF THE INVENTION

1. Field of the Invention

The present invention relates to an organosilane compound and an organosilica obtained from the organosilane compound.

2. Related Background Art

Studies have been conducted on various organosilane compounds and organosilicas obtained from the organosilane compounds. For example, the Journal of Organic Chemistry, Vol. 67, pp. 5279 to 5283, 2002 (Document 1) discloses an oligophenylene-based organosilane as an organosilica which can be utilized as a surface-treating agent. Moreover Document 1 discloses a triallylsilylbenzene derivative having a halogen substituent or a boranyl substituent, as an organosilane compound for producing an oligophenylene-based organosilane.

Additionally, Japanese Unexamined Patent Application Publication No. 2006-89588 (JP 2006-89588 A) discloses an organosilica obtained by hydrolysis and polycondensation of a certain organosilane compound, including an organosilane compound having a triallylsilyl group, in a solvent.

However, as for the organosilane compound described in Document 1, a synthesis of the organosilica through a hydrolysis reaction is not investigated. Moreover, a commonly-used organosilane compound having a trialkoxysilyl group is chemically unstable, and easily reacts with silica gel in the reaction system and with a minute amount of water in the air in the purification process during the synthesis. For this reason, it is necessary to adopt a process, such as filtration and distillation, under no-water conditions during the purification process. Accordingly, the synthesis process for the organosilane compound is limited. Furthermore, it is difficult to produce a mesostructured organosilica in relatively moderate reaction conditions in the case of using an organosilane compound having a triallylsilyl group. Additionally, it is difficult to use the organosilane compound described in the Document 1 or JP 2006-89588 A as a raw-material compound for producing an organosilica having a function, such as a refractive index controlling function, a light absorbing function, a light emitting function, and a charge transferring function.

SUMMARY OF THE INVENTION

The present invention has been made in consideration of the problems in the prior art. An object of the present invention is to provide an organosilane compound having a sufficiently high chemical stability, and being useful for a synthesis of a mesostructured organosilica as well as a synthesis of an organosilica having a function, such as a refractive index controlling function, a light absorbing function, a light emitting function, and a charge transferring function. Another object is to provide an organosilica obtained from the organosilane compound.

The present inventors have devoted themselves to keen studies so as to achieve the above object. As a result, the present inventors have found the following facts. Specifically, firstly, they have found that an organosilane compound containing a diallylalkoxysilyl group and a specific organic group containing a phenylene group, a biphenylylene group, a naphthylene group, a pyridylene group, a vinylene group, or an ethynylene group, can have a sufficiently high chemical stability to moisture in the air, and the like. Then, the present inventors have also found that the organosilane compound which is useful for a synthesis of an organosilica is derivatized readily by utilizing a commonly-used organic synthetic reaction, for example, a coupling reaction including Suzuki, Sonogashira, Negishi, Kumada-Tamao, Kosugi-Migita-Stille, Hiyama, and amination reactions. Thus, it became possible to easily synthesize a mesostructured organosilica and various organosilicas having a function, such as a refractive index controlling function, a light absorbing function, a light emitting function, and a charge transferring function. In this way, the present invention has been completed.

To be more specific, a first organosilane compound of the present invention is expressed by the following general formula (1):

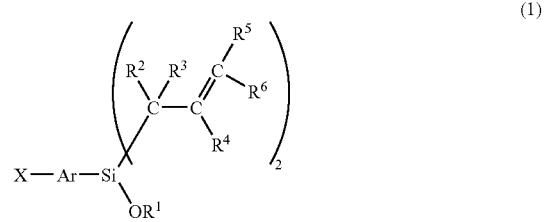

(wherein: Ar represents any one divalent aromatic organic group selected from the group consisting of a phenylene group, a biphenylylene group, a naphthylene group and a pyridylene group; $R^1$ represents any one of a hydrogen atom and alkyl groups having 1 to 4 carbon atoms; $R^2$ to $R^6$, which may be the same or different from each other, each represent any one selected from the group consisting of a hydrogen atom, a methyl group, an ethyl group, a propyl group, a butyl group, an isopropyl group, a pentyl group, a hexyl group, and a cyclohexyl group; and X represents any one reactive substituent selected from the group consisting of a halogen atom, a magnesium halide, a zinc halide, a stannyl group which may have a substituent, a boranyl group which may have a substituent, and a triflate group).

In the first organosilane compound of the present invention described above, Ar in the general formula (1) is preferably the phenylene group.

Moreover, in the first organosilane compound of the present invention, $R^1$ in the general formula (1) is preferably one selected from the group consisting of a methyl group and an ethyl group.

Furthermore, in the first organosilane compound of the present invention, X in the general formula (1) is preferably one selected from the group consisting of the halogen atom, the boranyl group, and the triflate group.

Additionally, a second organosilane compound of the present invention is expressed by the following general formula (2):

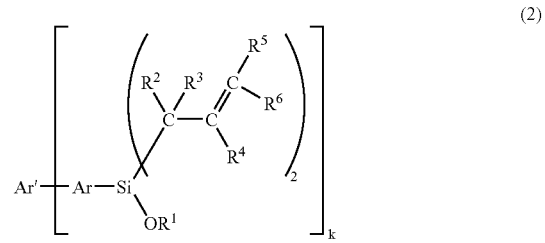

(where: Ar represents any one divalent aromatic organic group selected from the group consisting of a phenylene group, a biphenylylene group, a naphthylene group, and a pyridylene group; $R^1$ represents any one of a hydrogen atom and alkyl groups having 1 to 4 carbon atoms; $R^2$ to $R^6$, which may be the same or different from each other, each represent any one selected from the group consisting of a hydrogen atom, a methyl group, an ethyl group, a propyl group, a butyl group, an isopropyl group, a pentyl group, a hexyl group, and a cyclohexyl group; k represents an integer in a range from 1 to 6; and Ar' represents an aromatic organic group having a valency of k and containing at least one aromatic ring selected from the group consisting of a benzene ring, a naphthalene ring, an anthracene ring, a pyridine ring, a carbazole ring, and a fluorene ring).

In the second organosilane compound of the present invention, Ar in the general formula (2) is preferably one selected from the group consisting of a phenyl group, a methoxyphenyl group, a biphenyl group, and a methoxybiphenyl group, and is more preferably a methoxyphenyl group.

Moreover, in the second organosilane compound of the present invention, Ar in the general formula (2) is preferably the phenylene group.

Furthermore, in the second organosilane compound of the present invention, $R^1$ in the general formula (2) is preferably any one selected from the group consisting of a methyl group and an ethyl group.

A first organosilica of the present invention is obtained by polymerizing at least one of the first organosilane compounds of the present invention.

Moreover, a second organosilica according to the present invention is obtained by polymerizing at least one of the second organosilane compounds of the present invention.

According to the present invention, it is possible to provide an organosilane compound having a sufficiently high chemical stability, and being useful for a synthesis of a mesostructured organosilica as well as a synthesis of an organosilica having a function, such as a refractive index controlling function, a light absorbing function, a light emitting function, and a charge transferring function. It is also possible to provide an organosilica obtained from the organosilane compound.

DETAILED DESCRIPTION OF THE PREFERRED EMBODIMENTS

Figure 1:
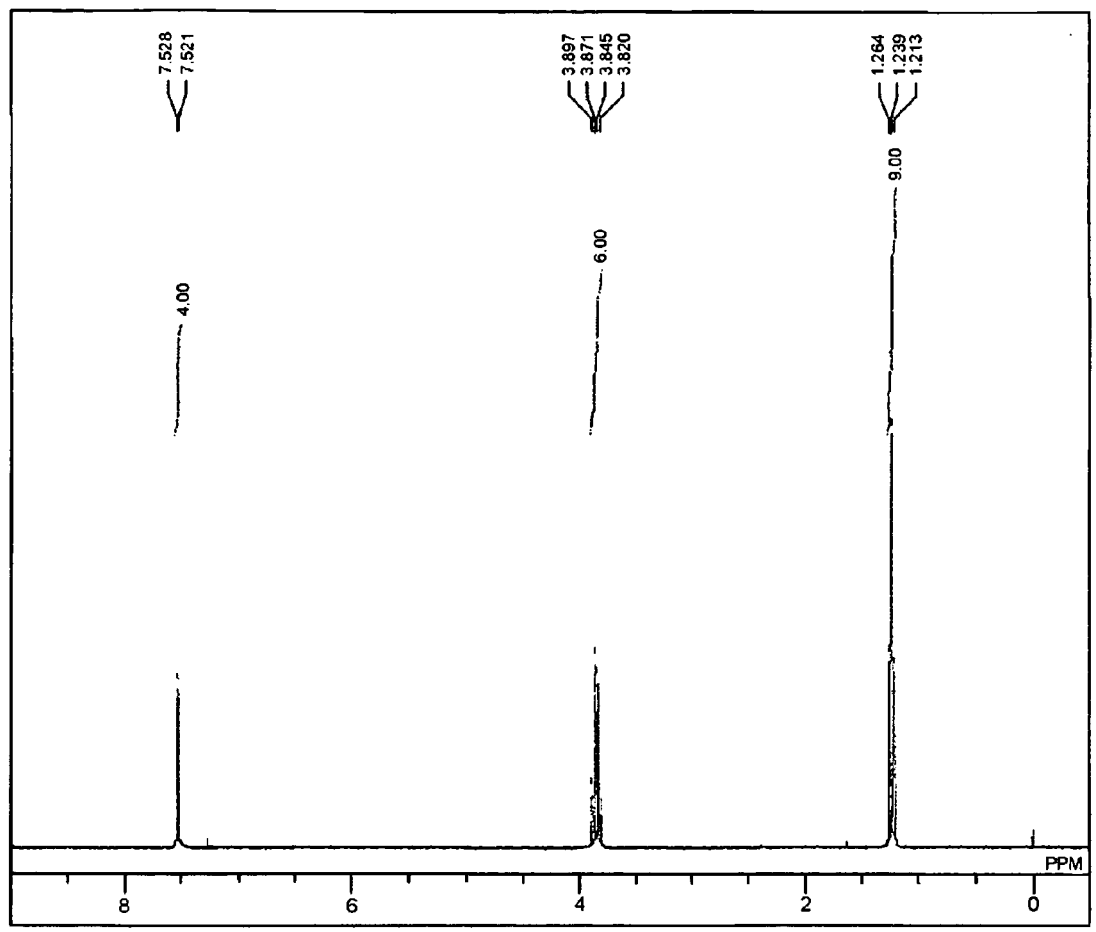
FIG. 1 is a graph showing a $^1$H NMR of 4-bromo-triethoxysilylbenzene obtained in Synthesis example 1.

Hereinafter, the present invention will be specifically described in line with preferred embodiments thereof.

[First Organosilane Compound]

A first organosilane compound of the present invention is expressed by the following general formula (1):

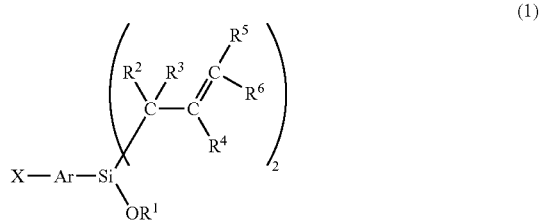

In the general formula (1), Ar represents any one divalent aromatic organic group selected from the group consisting of a phenylene group, a biphenylylene group, a naphthylene group, and a pyridylene group. Such a divalent aromatic organic group represented by Ar is preferably the phenylene group, the biphenylylene group, and the naphthylene group from the viewpoint of application to an optical functional material, and preferably the pyridylene group from the viewpoints of application to a catalysis and incorporation with a metal.

In the general formula (1), $R^1$ represents any one of a hydrogen atom and alkyl groups having 1 to 4 carbon atoms. Such an alkyl group having 1 to 4 carbon atoms represented by $R^1$ includes a methyl group, an ethyl group, a propyl group, an isopropyl group, a butyl group, a sec-butyl group, and a tert-butyl group. From the viewpoint of an efficient synthesis of an organosilica through hydrolysis and polycondensation reaction, the methyl group and the ethyl group are preferable.

Furthermore, in the general formula (1), the substituents represented by $R^2$ to $R^6$, which may be the same or different from each other, each represent a hydrogen atom, a methyl group, an ethyl group, a propyl group, a butyl group, an isopropyl group, a pentyl group, a hexyl group, or a cyclohexyl group. In the case where $R^2$ to $R^6$ are substituents other than these substituents, it is difficult for an allyl group having the substituent represented by $R^2$ to $R^6$ to be detached from the silica skeleton during the synthesis of an organosilica. As a result, it tends to be difficult to form a stable siloxane binding (Si—O—Si) at a sufficient level.

Moreover, in the general formula (1), X represents any one reactive substituent selected from the group consisting of a halogen atom, a magnesium halide, a zinc halide, a stannyl group which may have a substituent, a boranyl group which may have a substituent, and a triflate group. The stannyl group having such a substituent is not particularly limited, and may be, for example, a trimethyltin group, a triethyltin group, a tri-1-propyltin group, a tri-n-butyltin group, a triphenyltin group, a tricyclohexyltin group, or a triallyltin group. From the viewpoint of chemical stability, the trimethyltin group, thetriethyltin group, and the tri-n-butyltin group are preferable. Meanwhile, the example of the boranyl group having a substituent includes a dimethylboranyl group, a di(2,6-diethylphenyl)boranyl group, a di(2,6-diisopropylphenyl)boranyl group, a 9-borabicyclo[3,3,1]nonane group, a catechol boranyl group, and a pinacol boranyl group. From the viewpoint of chemical stability, the catechol boranyl group and the pinacol boranyl group are preferable.

Additionally, the substituent represented by X is preferably a halogen atom, a boranyl group, and a triflate group from the viewpoint of chemical stability.

Next, description will be given of a preferred method of producing the first organosilane compound of the present invention.

The example of the preferred method of producing the first organosilane compound is as follows. At first, a raw-material compound expressed by the following general formula (3):

$$\text{A—Ar—A} \qquad (3)$$

(where: Ar represents any one divalent aromatic organic group selected from the group consisting of a phenylene group, a biphenylylene group, a naphthylene group, and a pyridylene group; and As, which may be the same or different from each other, each represent a halogen atom) is caused to react with a silane compound expressed by the following general formula (4):

$$\text{H—Si(OR}^1)_3 \qquad (4).$$

Thus, obtained is a precursor compound expressed by the following general formula (5):

$$\text{A—Ar—Si(OR}^1)_3 \qquad (5)$$

(where, Ar represents any one divalent aromatic organic group selected from the group consisting of a phenylene group, a biphenylylene group, a naphthylene group and a pyridylene group; A represents the halogen atom; and $R^1$ represents any one of a hydrogen atom and alkyl groups having 1 to 4 carbon atoms). Then, the precursor compound is allylated so that two of the substituents denoted by —$OR^1$ in the precursor compound expressed by the general formula (5) can be substituted for allyl groups. Consequently, a first organosilane compound expressed by the general formula (1) where X is halogen is obtained.

The $R^1$ or Ar in the general formulae (3) to (5) is the same as $R^1$ or Ar in the general formula (1). The As in the general formulae (3) and (5) represent halogen atoms, and are preferably a boron atom or an iodine atom since these elements are more reactive.

Meanwhile, the step of obtaining the precursor compound expressed by the general formula (5) is not particularly limited, as long as the precursor compound is obtained by causing the raw-material compound expressed by the general formula (3) to react with the silane compound expressed by the general formula (4). Such a step is exemplified as follows. Specifically, at first, the raw-material compound expressed by the general formula (3) is mixed with a [Rh(CH$_3$CN)$_2$(cod)]BF$_4$ complex and Bu$_4$NI under a nitrogen atmosphere and room temperature, and then added with a solvent to obtain a mixed liquid. Subsequently, the mixed liquid is further added with triethylamine and dimethylformamide (DMF), thus a mixed solution is obtained. Thereafter, the silane compound expressed by the general formula (4) is added dropwise thereto at 0° C., and thoroughly stirred for approximately 1 hour to 2 hours at 80° C. to obtain a crude product. After that, the solvent is removed thereby to obtain the precursor compound.

The solvent mixed with the raw-material compound expressed by the general formula (3) includes DMF, acetonitrile, N-methyl-2-pyrrolidone (NMP), and dioxane.

The method for allylation of the precursor compound is not particularly limited, and a known method can be adopted as appropriate. Such a method is exemplified as follows. Specifically, at first, after the precursor compound is obtained as described above, an allylating agent, such as allylmagnesium bromide [CH$_2$=CH—CH$_2$MgBr], is added thereto under a nitrogen atmosphere at approximately −10° C. to 0° C. to obtain a mixture. Then, the mixture thus obtained is stirred under a room temperature condition (approximately 25° C.) for approximately 5 hours to 20 hours. Subsequently, the mixture is cooled at approximately −10° C. to 0° C., and an organic layer is separated therefrom. After that, the organic layer is washed with a washing solution (for example, NaHCO$_3$ and NaCl) and dried. Consequently, the precursor compound is allylated.

Moreover, another preferred method of producing the first organosilane compound of the present invention is exemplified as follows. After the first organosilane compound expressed by the general formula (1) where X represents halogen is produced as described above, the halogen group in the organosilane compound is substituted by a stannyl group which may have a substituent or by a boranyl group which may have a substituent. Thereby, a first organosilane compound is produced as expressed by the general formula (1) where X is the stannyl group which may have a substituent or the boranyl group which may have a substituent.

The method of substituting the halogen atom for the stannyl group which may have a substituent or the boranyl group which may have a substituent is not particularly limited, as long as these substitutions are possible to be performed. It is possible to adopt a known method such as the Grignard reaction, as appropriate.

Next, description will be given of another preferred method of producing the first organosilane compound of the present invention. The example of this preferred method of producing the first organosilane compound of the present invention is as follows. At first, a raw-material compound expressed by the following general formula (6)

$$\text{HO—Ar—A} \qquad (6)$$

(where: Ar represents any one divalent aromatic organic group selected from the group consisting of a phenylene group, a biphenylylene group, a naphthylene group, and a pyridylene group; A represents a halogen atom) is caused to react with a compound expressed by the above general formula (4). Thus, obtained is a precursor compound expressed by the following general formula (7):

$$\text{HO—Ar—Si(OR}^1)_3 \qquad (7)$$

(where: Ar represents any one divalent aromatic organic group selected from the group consisting of a phenylene group, a biphenylylene group, a naphthylene group, and a pyridylene group; $R^1$ represents any one of a hydrogen atom and alkyl groups having 1 to 4 carbon atoms). Then, two of the substituents denoted by —$OR^1$ in the precursor compound expressed by the general formula (7) are substituted for allyl groups. Subsequently, a hydroxyl group thereof is substituted for a triflate group. Consequently, a first organosilane compound expressed by the general formula (1) where X is a triflate group is obtained.

The $R^1$ or Ar in the general formulae (4), (6) and (7) is the same as $R^1$ or Ar in the general formula (1). The A in the general formula (6) represents a halogen atom, and is preferably a boron atom or an iodine atom since these elements are more reactive.

The method of substituting the hydroxyl group in the compound after the allylation for the triflate group is not particularly limited, and it is possible to adopt a known method as appropriate.

Hereinabove, a description has been given of the preferred method of producing the organosilane compound expressed by the general formula (1). However, the production method is not peculiarly limited. It is possible to adopt other methods which allow the production of the organosilane compound expressed by the general formula (1), as appropriate.

[Second Organosilane Compound]

A second organosilane compound according to the present invention is expressed by the following general formula (2):

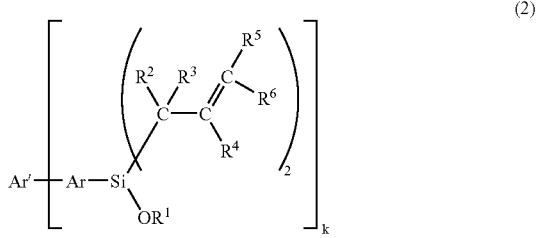

(wherein: Ar represents any one divalent aromatic organic group selected from the group consisting of a phenylene group, a biphenylylene group, a naphthylene group, and a pyridylene group; $R^1$ represents any one of a hydrogen atom and alkyl groups having 1 to 4 carbon atoms; $R^2$ to $R^6$, which may be the same or different from each other, each represent one selected from the group consisting of a hydrogen atom, a methyl group, an ethyl group, a propyl group, a butyl group, an isopropyl group, a pentyl group, a hexyl group, and a cyclohexyl group; k represents an integer in a range from 1 to 6; and Ar' represents an aromatic organic group having a valency of k and containing at least one aromatic ring selected from the group consisting of a benzene ring, a naphthalene ring, an anthracene ring, a pyridine ring, a carbazole ring, and a fluorene ring).

In the general formula (2), Ar and $R^1$ to $R^6$ are the same as Ar and $R^1$ to $R^6$ described in the first organosilane compound of the present invention.

In the general formula (2), k represents an integer in a range from 1 to 6. The value of k is preferably in a range from 2 to 6 from the viewpoint that the organosilane compound is used as a material to synthesize an organosilica having been moderately bridged.

In the general formula (2), Ar' represents an aromatic organic group having a valency of k and containing at least one aromatic ring selected from the group consisting of a benzene ring, a naphthalene ring, an anthracene ring, a pyridine ring, a carbazole ring and a fluorene ring. The aromatic organic group having a valency of k represented by Ar' is not particularly limited, as long as the aromatic organic group contains at least one aromatic ring selected from the group consisting of a benzene ring, a naphthalene ring, an anthracene ring, a pyridine ring, a carbazole ring, and a fluorene ring. Such aromatic organic groups having a valency of k, which, for example, may each include a substituent, include a phenyl group, a biphenyl group, an anthryl group, a pyridyl group, a carbazole group, a fluorene group, a phenylene group, a biphenylene group, a terphenyl group, a triphenylene group, a triphenylbenzene group, a tetraphenylpyrene group, and a hexaphenylbenzene group. Meanwhile, the examples of the substituent, which the aromatic organic group may include, are a methyl group, an ethyl group, a methoxy group, an ethoxy group, a cyano group, a nitro group, a hydroxyl group, and a halogen group.

Among these aromatic organic groups having a valency of k represented by Ar', a phenyl group, a methoxyphenyl group, a biphenyl group, and a methoxybiphenyl group are preferred from the viewpoint of synthesizing chemically-stable optical and electronic functional materials.

Next, description will be given of a preferred method of producing the second organosilane compound of the present invention.

The example of the preferred method of producing the second organosilane compound is as follows. Firstly, the first organosilane compound expressed by the general formula (1) is caused to react with a compound expressed by the following general formula (8):

(where: k represents an integer in a range from 1 to 6; Ar' represents an aromatic organic group having a valency of k and containing at least one aromatic ring selected from the group consisting of a benzene ring, a naphthalene ring, an anthracene ring, a pyridine ring, a carbazole ring, and a fluorene ring; and Z represents a functional group, such as a boronic acid group, a halogen atom, a stannyl group, a triflate group, a magnesium halide group, and a zinc halide group). Thus, the substituent denoted by X in the first organosilane compound expressed by the general formula (1) is substituted by the substituent denoted by —Ar' in the general formula (8). Consequently, a second organosilane compound is obtained.

Ar' and k in the general formula (8) are the same as Ar' and K in the general formula (2). The Z in the general formula (8) represents a functional group, such as a boronic acid group, a halogen atom, a stannyl group, a triflate group, a magnesium halide group, and a zinc halide group. As the Z in the general formula (8), a boronic acid group, a halogen atom, and a stannyl group is preferable, since these functional groups are easily adopted in an aryl coupling reaction.

Meanwhile, the method of causing the first organosilane compound of the present invention to react with the compound expressed by the general formula (8) is not particularly limited, as long as the substituent denoted by X in the first organosilane compound expressed by the general formula (1) is substituted by the substituent denoted by —Ar' in the general formula (8). It is possible to adopt a known method as appropriate.

Hereinabove, the description has been given of the preferred method of producing the organosilane compound expressed by the general formula (2). However, the production method is not limited to the above-described method. It is possible to adopt other methods which allow the production of the organosilane compound expressed by the general formula (2), as appropriate.

[First and Second Organosilicas]

A first organosilica of the present invention is obtained by polymerizing at least one of the first organosilane compounds of the present invention. A second organosilica of the present invention is obtained by polymerizing at least one of the second organosilane compounds of the present invention.

When at least one of the first organosilane compounds and/or at least one of the second organosilane compounds of the present invention is polymerized (hydrolyzed and polycondensed), the allyl group and the group represented by the $OR^1$ in the first and/or second organosilane compounds of the present invention are fundamentally detached, and a siloxane binding (Si—O—Si) is formed through the hydrolysis and the subsequent polycondensation reaction in the detachment portion.

As described above, the organosilica obtained by polymerizing at least one of the first and/or second organosilane compounds of the present invention has an organic groups including Ar and/or Ar', a silicon atom (Si), and an oxygen atom (O) as the main components of the skeleton. The organosilica has a highly-bridged mesh structure.

The methods of polymerizing at least one of the first organosilane compounds of the present invention and/or at least one of the second organosilane compounds of the present invention is not particularly limited. In a preferred method, it is preferable that at least one of the first organosilane compounds of the present invention and/or at least one of the second organosilane compounds of the present invention be hydrolyzed and polycondensed under the presence of an acidic or basic catalyst upon using water or a mixture solvent of water and an organic solvent as the solvent. The organic solvent preferably used includes alcohol, acetone, and the like. When the mixture solvent is used, the content of the organic solvent is preferably in a range from approximately 5% by weight to 90% by weight. The acidic catalyst to be used may be, for example, a mineral acid, such as hydrochloric acid, nitric acid, and sulfuric acid. When the acidic catalyst is used, the solution is preferably acidic having a pH of 6 or below (more preferably in a range from 2 to 5). In addition, the basic catalyst to be used may be, for example, sodium hydroxide, ammonium hydroxide, and potassium hydroxide. When the basic catalyst is used, the solution is preferably basic having a pH of 8 or higher (more preferably in a range from 9 to 11).

The content of the first and/or second organosilane compounds of the present invention in the polymerization step is preferably approximately 0.0055 mol/L to 0.33 mol/L in terms of silica concentration. The reaction conditions (temperature, duration, and the like) in the polymerization step are not particularly limited, and are selected appropriately in accordance with a type of the first and second organosilane compounds to be used or a type of organosilica to be obtained. In general, it is preferable that the first or second organosilane compounds of the present invention be hydrolyzed and polycondensed at approximately 0° C. to 100° C. for 1 hour to 48 hours.

Furthermore, the organosilica obtained by polymerizing at least one of the first organosilane compounds of the present invention and/or at least one of the second organosilane compounds of the present invention generally has an amorphous structure. However, the organosilica can have a periodic structure based on an ordered arrangement of the organic groups (Ar and/or Ar') in accordance with the synthesis conditions. Although such periodicity depends on the molecular length of the organosilane compound to be used, the periodicity of the periodic structure is preferably 5 nm or below. Such a periodic structure is maintained even after at least one of the first organosilane compounds of the present invention or at least one of the second organosilane compounds of the present invention is polymerized. The formation of the periodic structure can be recognized by a peak appeared in a region where the d value is 5 nm or below in the X-ray diffraction (XRD) measurement. Even when such a peak is not recognized in the XRD measurement, the periodic structure is partially formed in some cases. Such a periodic structure is generally formed with a layered structure to be described below, but not limited to this case.

The preferable synthesis conditions for forming such a periodic structure based on the ordered arrangement of the organic groups include various conditions as follows.

(i) The periodic structure is formed by the interaction among the first organosilane compounds and/or second organosilane compounds of the present invention. Thus, it is preferable that an organic group represented by Ar and/or Ar' included in the first or second organosilane compounds of the present invention have a higher molecular weight so that the interaction among the first and/or second organosilane compounds of the present invention can be increased.

(ii) The solution preferably has a pH of 1 to 3 (acidic) or a pH of 10 to 12 (basic), and more preferably has a pH of 10 to 12 (basic).

Moreover, in the methods of producing the first and second organosilicas of the present invention, pores can be formed in the obtained organosilicas by adding a surfactant to a reaction mixture for polymerization (hydrolysis and polycondensation) of at least one of the first organosilane compounds of the present invention and/or at least one of the second organosilane compounds of the present invention. In other words, the micelle or liquid crystal structure of the surfactant serves as a template to form a porous material having pores.

It is preferable to use a surfactant together with the first and/or second organosilane compounds of the present invention, since a mesoporous material having a mesopore with a central pore diameter of 1 nm to 30 nm in a pore diameter distribution curve can be obtained by utilizing of the surfactant. Note that the central pore diameter is a pore diameter at the maximum peak of the curve (pore diameter distribution curve). In this curve, values (dV/dD) obtained by differentiating a pore volume (V) by a pore diameter (D) are plotted to corresponding pore diameter (D). The central pore diameter can be obtained by the method described below. Specifically, the porous material is cooled to a liquid nitrogen temperature (−196° C.). Then, a nitrogen gas is introduced to determine an absorbed amount of the nitrogen gas with a volumetrical method or a gravimetrical method. Subsequently, the pressure of the nitrogen gas being introduced is gradually increased. Thereafter, the amount of nitrogen gas adsorbed is plotted to each equilibrium pressure thereby an adsorption isotherm is obtained. Using the adsorption isotherm, a pore diameter distribution curve can be calculated by a calculation method, such as a Cranston-Inklay method, a Pollimore-Heal method, and a BJH method.

It is preferable that at least 60% of the total pore volume of the mesoporous material be included within a range of ±40% of the central pore diameter in the pore diameter distribution curve. Such a mesoporous material satisfying this condition has highly uniform diameters of the pores thereof. The specific surface area of the mesoporous material is not particularly limited, and is preferably 700 m$^2$/g or more. The specific surface area can be calculated as a BET specific surface area based on the adsorption isotherm by a BET isothermal adsorption equation.

Furthermore, the mesoporous material preferably has one or more peaks at a diffraction angle corresponding to the d value of 1.5 nm to 30.5 nm in the XRD pattern. An X-ray diffraction peak indicates that a periodic structure of a d value corresponding to the peak angle is present in the sample. Accordingly, the fact that one or more peaks are present at a diffraction angle corresponding to the d value of 1.5 nm to 30.5 nm means that the pores are orderly arranged at intervals in a range from 1.5 nm to 30.5 nm.

The pores in the mesoporous material are formed not only on the surface of the porous material but also in the inside thereof. The pore arrangement state (pore arrangement structure, or simply structure) in the porous material is not particularly limited, and is preferably of a 2d-hexagonal structure, a 3d-hexagonal structure, or a cubic structure. The pore arrangement structure may be a disordered pore arrangement structure.

In this case, the phrase that the porous material has a hexagonal pore arrangement structure means that the arrangement of the pores is of a hexagonal structure (see: S.

Inagaki et. al., J. Chem. Soc., Chem. Commun., p. 680 (1993); S. Inagaki et al., Bull. Chem. Soc. Jpn., 69, p. 1449 (1996); Q. Huo et al., Science, 268, p. 1324 (1995)). Moreover, the phrase that the porous material has a cubic pore arrangement structure means that the arrangement of the pores is of a cubic structure (see: J. C. Vartuli et al., Chem. Mater., 6, p. 2317 (1994); Q. Huo et al., Nature, 368, p. 317 (1994)). In addition, the phrase that the porous material has a disordered pore arrangement structure means that the arrangement of the pores is irregular (see: P. T. Tanev et al., Science, 267, p. 865 (1995); S. A. Bagshaw et al., Science, 269, p. 1242 (1995); R. Ryoo et al., J. Phys. Chem., 100, p. 17718 (1996)). Furthermore, the cubic structure preferably has a Pm-3n, Ia-3d, Im-3m, or Fm-3m symmetrical property. The symmetrical property is to be determined on the basis of the notation of a space group.

In the case where the first and second organosilicas of the present invention have pores, the pores allow the porous materials to adsorb (by physical adsorption and/or chemical bonding) a metal having a catalytic function and a functional element, such as a fluorescent compound and a pigment.

The surfactant used in obtaining the mesoporous material is not particularly limited, and may be any one of cationic, anionic, and non-ionic surfactants. To be more specific, the surfactant includes: a chloride, a bromide, an iodide, and a hydroxide of alkyltrimethylammonium, alkyltriethylammonium, dialkyldimethylammonium, benzyl ammonium, and the like; and a fatty acid salt, alkylsulfonate, alkylphosphate, polyethylene oxide-based non-ionic surfactant, primary alkyl amine, and the like. These surfactants are used alone or in combination of two or more kinds.

Among the above surfactants, the polyethylene oxide-based non-ionic surfactant includes ones having a hydrocarbon group as a hydrophobic component and a polyethylene oxide as a hydrophilic component, for example. Such a surfactant preferably used is expressed by a general formula, for example, $C_nH_{2n+1}(OCH_2CH_2)_mOH$ where n is 10 to 30 and m is 1 to 30. In the place of such a surfactant, esters of sorbitan and a fatty acid, such as oleic acid, lauric acid, stearic acid, and palmitic acid, or compounds formed by adding polyethylene oxide to these esters can also be used.

Furthermore, a triblock copolymer of polyalkylene oxide can also be used as the surfactant. Such a surfactant includes one made of polyethylene oxide (EO) and polypropylene oxide (PO), and expressed by a general formula $(EO)_x(PO)_y(EO)_x$. Here, x and y are the numbers of repetitions of EO and PO, respectively. It is preferable that x be in a range from 5 to 110 and y be in a range from 15 to 70, and more preferable that x be in a range from 13 to 106 and y be in a range from 29 to 70. The triblock copolymer includes $(EO)_{19}(PO)_{29}(EO)_{19}$, $(EO)_{13}(PO)_{70}(EO)_{13}$, $(EO)_5 (PO)_{70} (EO)_5$, $(EO)_{13} (PO)_{30} (EO)_{13}$, $(EO)_{20} (PO)_{30} (EO)_{20}$, $(EO)_{26} (PO)_{39} (EO)_{26}$, $(EO)_{17} (PO)_{56} (EO)_{17}$, $(EO)_{17} (PO)_{58} (EO)_{17}$, $(EO)_{20} (PO)_{70} (EO)_{20}$, $(EO)_{80} (PO)_{30} (EO)_{80}$, $(EO)_{106} (PO)_{70} (EO)_{106}$, $(EO)_{100} (PO)_{39} (EO)_{100}$, $(EO)_{19}(PO)_{33} (EO)_{19}$ and $(EO)_{26} (PO)_{36} (EO)_{26}$. These triblock copolymers are available from BASF Group, Sigma-Aldrich Corp., and the like. The triblock copolymer having desired x and y values can also be obtained in a small-scale production level.

It is also possible to use a star diblock copolymer formed by binding two chains of a polyethylene oxide (EO) chain-polypropylene oxide (PO) chain to each of two nitrogen atoms of ethylenediamine. Such a star diblock copolymer includes one expressed by a general formula $((EO)_x(PO)_y)_2NCH_2CH_2N((PO)_y(EO)_x)_2$ where x and y represent the numbers of repetitions of EO and PO, respectively. It is preferable that x be in a range from 5 to 110 and y be in a range from 15 to 70, and more preferable that x be in a range from 13 to 106 and y be in a range from 29 to 70.

Among the above surfactants, a salt (preferably a halide salt) of alkyltrimethylammonium $[C_pH_{2p+1}N(CH_3)_3]$ is preferably used because the mesoporous material having a high crystallinity can be obtained with this surfactant. In this case, the alkyltrimethylammonium preferably has an alkyl group having 8 to 22 carbon atoms. The alkyltrimethylammoniums are, for example, octadecyltrimethylammonium chloride, hexadecyltrimethylammonium chloride, tetradecyltrimethylammonium chloride, dodecyltrimethylammonium bromide, decyltrimethylammonium bromide, octyltrimethylammonium bromide, and docosyltrimethylammonium chloride.

In order to produce the first or second organosilicas of the present invention using the above-described surfactant, the first and/or second organosilane compound of the present invention are firstly hydrolyzed and polycondensed in the above-described solvent containing the surfactant. Thus, obtained is a porous material precursor which is an organosilica containing the surfactant. In this step, the concentration of the surfactant in the solution is preferably in a range from 0.05 mol/L to 1 mol/L. When the surfactant concentration is less than the lower limit, the formation of the pores tend to be incomplete. On the other hand, when the concentration exceeds the upper limit, the amount of the surfactant which is unreacted and remains in the solution is increased, and therefore the uniformity of the pores tends to be decreased.

Then, the surfactant contained in the porous material precursor thus obtained is removed to obtain a porous organosilica. In this step, the surfactant can be removed in the following methods, for example: (i) a method of removing the surfactant in which the porous material is immersed in an organic solvent (for example, ethanol) having a high solubility to the surfactant; (ii) a method of removing the surfactant in which the porous material precursor is calcined at 250° C. to 550° C.; (iii) an ion-exchange method in which the porous material precursor is immersed in an acidic solution and heated to exchange the surfactant with hydrogen ions.

Furthermore, the first and second organosilicas of the present invention thus obtained can acquire a function, such as a refractive index controlling function, a light absorbing function, a light emitting function, and a charge transferring function, when a type of the organosilane compound used (particularly, a type of organic group represented by Ar or Ar') is appropriately selected. Therefore, it is possible to suitably utilize the first and second organosilicas of the present invention as a fluorescent material, a charge-transfer material, a thin film, and the like.

Moreover, the first and second organosilicas of the present invention may be used in a powder form without any modification, but may be used after being molded as necessary. The molding means is not limited, but preferably is extrusion, tablet molding, tumbling granulation, compression molding, cold isostatic pressing (CIP), and the like. The form of the organosilicas which can be determined in accordance with a method and a place to be used includes columnar, granular, spherical, honeycomb, asperity, and corrugated forms.

Furthermore, the first and second organosilicas of the present invention can be made into a thin-film form by the following method, for example. In order to obtain such a thin-film organosilica, the first and/or second organosilane compounds of the present invention are firstly stirred in an acidic solution (for example, an aqueous solution, such as hydrochloric acid and a nitric acid, or an alcohol solution) for a partial polymerization reaction (partial hydrolysis and partial polycondensation reaction) to obtain a sol solution including the partial polymer. Since the hydrolysis reaction of the first and second organosilane compounds of the present invention is likely to take place in a region low in pH, it is possible to accelerate the partial polymerization by reducing the pH of the reaction system. At this point, the pH is preferably 2 or below, and more preferably 1.5 or below. Moreover, the reaction temperature can be approximately 15° C. to 25° C., and the reaction duration can be approximately 30 minutes to 90 minutes.

Subsequently, the sol solution thus obtained is coated on a board, and thereby a thin-film organosilica is produced. The method of coating a board with the sol solution is not particularly limited, and it is possible to adopt various coating methods as appropriate. The example of the coating method includes: a coating method with a bar coater, roll coater, gravure coater, or the like; and a method utilizing a dip coating, spin coating, spray coating, or the like. Additionally, it is possible to form a patterned organosilica on a board by coating the sol solution with an inkjet method.

Thereafter, the obtained thin film is heated to approximately 70° C. to 150° C. and dried to accelerate the polycondensation reaction of the partial polymer. Thereby, a three-dimensional bridged structure is preferably formed. Note that the addition of the above-described surfactant to the sol solution enables the ordered pore structure to be formed in the thin-film organosilica.

EXAMPLES

Hereinafter, the present invention will be more specifically described on the basis of examples and comparative examples. However, the present invention is not limited to the following examples.

Synthesis Example 1

4-bromo-triethoxysilylbenzene was Prepared as Follows

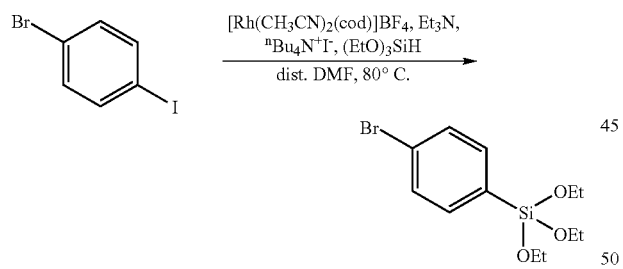

At first, a mixture of 4-iodo-bromobenzene (2.60 g, 9.19 mmol), t-butylammoniumiodido (3.39 g, 9.18 mmol) and [Rh(cod)(CH$_3$CN)$_2$] (105 mg, 0.277 mmol) was added with dimethylformamide (DMF: 26 mL) and triethylamine (2.56 mL, 18.4 mmol). Then, triethoxysilane (1.87 mL, 10.1 mmol) was added dropwise thereto at 0° C. The resultant mixture was stirred under a nitrogen atmosphere at 80° C. for one hour to obtain a reaction mixture. Subsequently, a solvent in the reaction mixture was distilled with a vacuum pump. Under a nitrogen atmosphere, the residue was extracted with ether, filtered with celite, and concentrated to obtain a crude product. Thereafter, the crude product thus obtained was purified by Kugel distillation, and thereby 4-bromo-triethoxysilylbenzene was obtained (2.38 g, 81% yield).

The obtained compound was subjected to a $^1$H NMR measurement. FIG. 1 shows a graph of the obtained NMR. From the NMR measurement result shown in FIG. 1, it was confirmed that the obtained compound was 4-bromo-triethoxysilylbenzene.

Example 1

4-bromo-diallylethoxysilylbenzene was Prepared as Follows

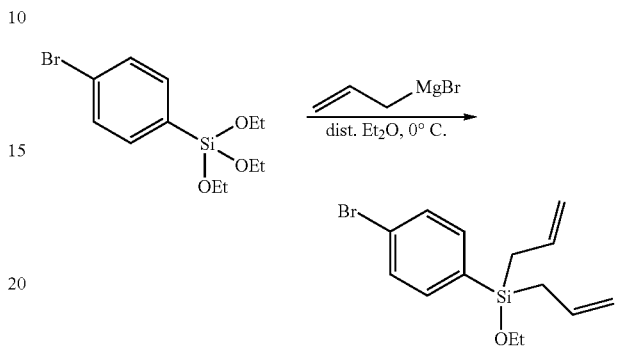

At first, the 4-bromo-triethoxysilylbenzene (4.74 g, 14.8 mmol) obtained in Synthesis example 1 was added dropwise with 1 mol/L of allylmagnesium bromide (59.4 mmol (solvent: ether), 59.4 mL) at 0° C. The mixture was stirred under a nitrogen atmosphere at room temperature overnight to obtain a reaction mixture. Subsequently, the obtained reaction mixture was neutralized with 10% by mass of an HCl solution. Thereafter, the organic layer was extracted with ether. The collected organic layer was washed with a saturated sodium acid carbonate solution (sat.NaHCO$_3$) and a saturated sodium chloride solution (sat.NaCl). After that, the obtained organic layers were dried with anhydrous magnesium sulfate (MgSO$_4$), filtered, and concentrated to obtain a crude product. The crude product thus obtained was purified by Kugel distillation, and thereby 4-bromo-diallylethoxysilylbenzene was obtained (4.20 g, 90.7% yield).

Figure 2:
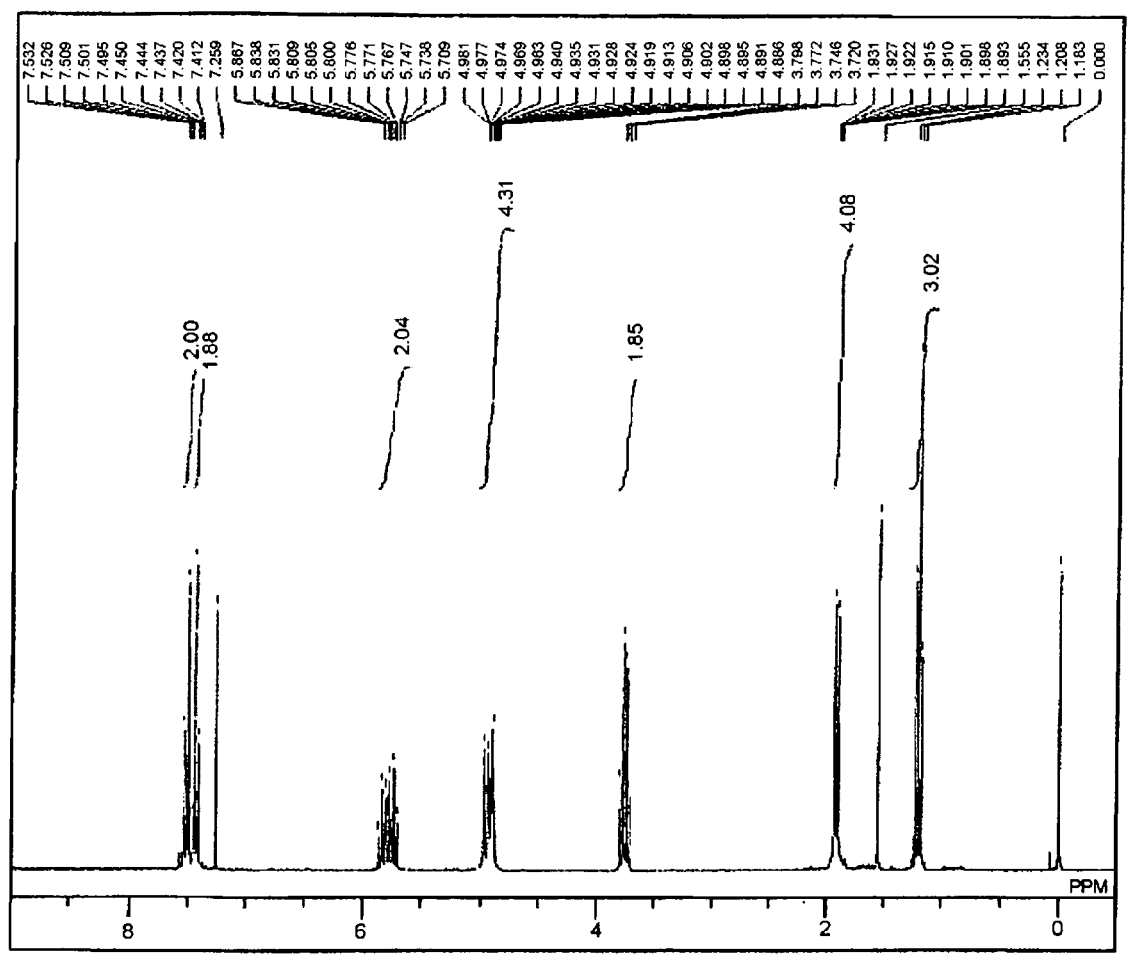
FIG. 2 is a graph showing a $^1$H NMR of 4-bromo-diallylethoxysilylbenzene obtained in Example 1.
Figure 3:
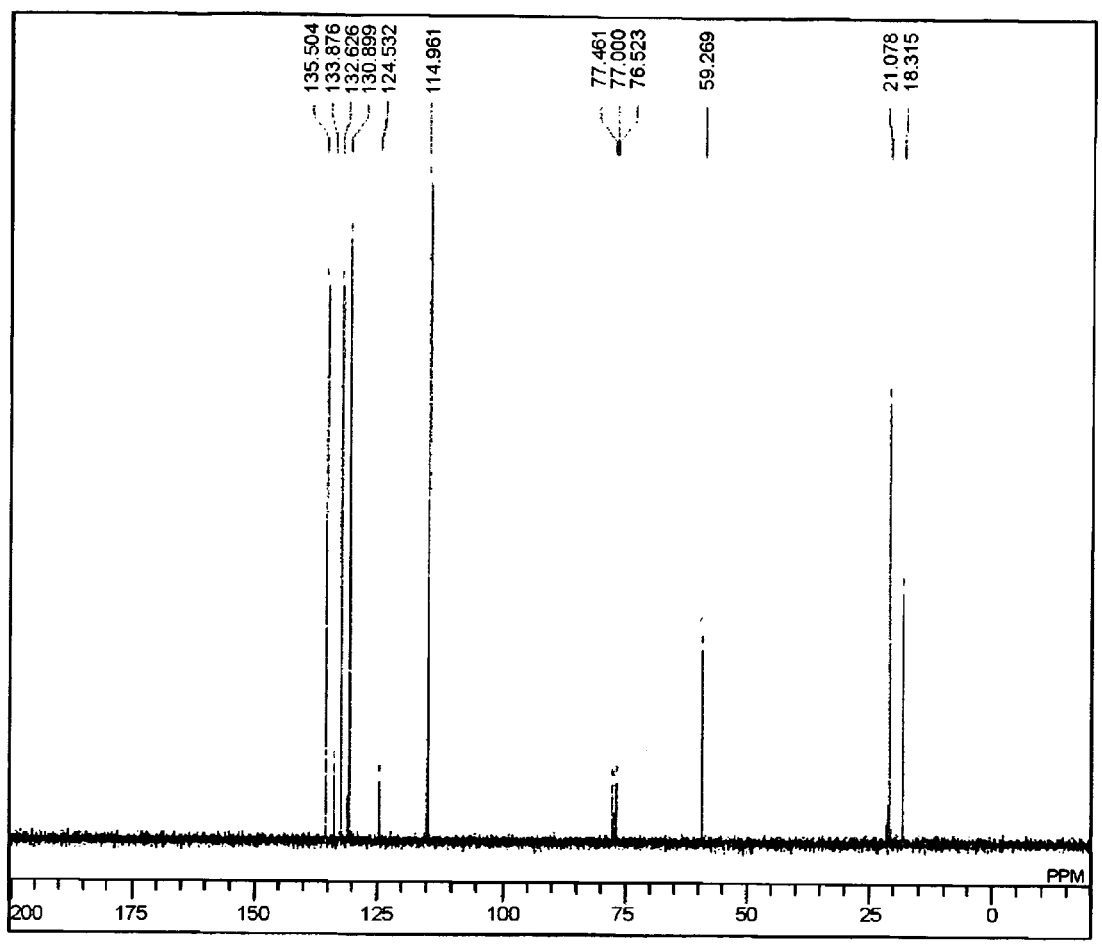
FIG. 3 is a graph showing a $^{13}$C NMR of 4-bromo-diallylethoxysilylbenzene obtained in Example 1.

The obtained compound was subjected to $^1$H NMR and $^{13}$C NMR measurements. FIGS. 2 and 3 show graphs of the obtained NMRs. From the NMR measurement results shown in FIGS. 2 and 3, it was confirmed that the obtained compound was 4-bromo-diallylethoxysilylbenzene.

Synthesis Example 2

4-(triethoxysilyl)iodobenzene was Prepared as Follows

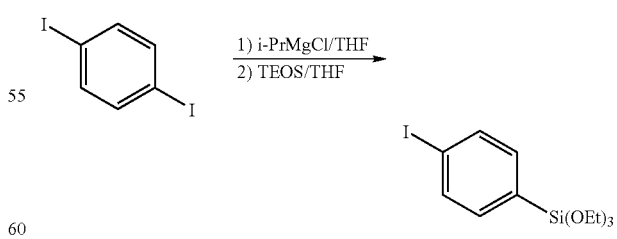

At first, a mixed solution of 1,4-diiodobenzene (15 g, 45.6 mmol) and a distilled tetrahydrofuran solution (dist.THF: 114 mL) was added dropwise with 2 mol/L of i-PrMgCl (24 mL (solvent: THF), 48 mmol) at −30° C. Then, the resultant mixture was stirred under a nitrogen atmosphere at −30° C. for 5.5 hours to obtain a reaction solution. Subsequently, the reaction solution was added dropwise (3 drops per second) using a cannula into a mixed solution of tetraethoxysilane (TEOS: 60.6 mL, 272 mmol) and dist.THF (90 mL), which was cooled to −30° C. Thereafter, the resultant mixed solution was stirred at −30° C. for one hour, and further stirred at room temperature for 44 hours to obtain a reaction mixture. After that, the obtained reaction mixture was added with ether (100 ml), and washed with distilled water (dist.H$_2$O). Then, the aqueous layer was extracted with ether. The collected organic layers were washed with sat.NaCl, dried with MgSO$_4$), filtered and concentrated to obtain a crude product. Thereafter, the crude product thus obtained was purified by distillation under a reduced pressure (1.5 mmHg, 120° C.), and thereby 4-(triethoxysilyl)iodobenzene was obtained (10.2 g, 61% yield).

The obtained compound was subjected to $^1$H NMR and $^{13}$C NMR measurements. The obtained results are shown below.
$^1$H NMR (CDCl$_3$) δ 7.73 (dd, J=7.8 Hz, 1.4 Hz, 2H), 7.39 (d, J=7.8 Hz, 1.4 Hz, 2H), 3.88 (q, J=7.3 Hz, 6H), 1.24 (t, J=7.3 Hz, 9H).

$^{13}$C NMR (CDCl$_3$) δ 137.0, 136.3, 130.4, 97.8, 58.8, 18.1. From the NMR measurement results, it was confirmed that the obtained compound was 4-(triethoxysilyl)iodobenzene.

Example 2

4-(diallylethoxysilyl)iodobenzene was Prepared as Follows

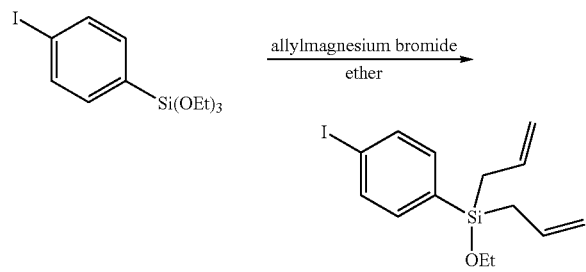

At first, the 4-(triethoxysilyl)iodobenzene (9.4 g, 25.7 mmol) obtained in Synthesis example 2 was added dropwise with 1 mol/L of allylmagnesium bromide (77 ml (solvent: ether), 77 mmol) at 0° C., and then stirred under a nitrogen atmosphere at room temperature for 13 hours to obtain a mixture product. Subsequently, the mixture product was added with 10% by mass of an HCl solution to terminate the reaction. The pH of the aqueous layer was adjusted to 4 with 10% by mass of an HCl solution. Thereafter, the organic layer was separated therefrom and the aqueous layer was extracted with ether. After that, the collected organic layer was washed with sat.NaHCO$_3$ and sat.NaCl, dried with MgSO$_4$, filtered, and concentrated to obtain a crude product. Then, the crude product thus obtained was separated and purified by silica gel column chromatography (hexane/EtOAc=20/1), and thereby 4-(diallylethoxysilyl)iodobenzene was obtained (9.0 g, 98% yield).

The obtained compound was subjected to $^1$H NMR and $^{13}$C NMR measurements. The obtained results are shown below.
$^1$H NMR (CDCl$_3$) δ 7.72 (d, J=8.1 Hz, 2H), 7.29 (d, J=8.1 Hz, 2H), 5.87-5.71 (m, 2H), 4.98-4.89 (m, 4H), 3.75 (q, J=6.8 Hz, 4H), 1.91 (d, J=8.1 Hz, 4H), 1.20 (t, J=6.8 Hz, 3H).

$^{13}$C NMR (CDCl$_3$) δ 136.9, 135.6, 134.5, 132.7, 115.0, 97.1, 59.4, 21.1, 18.4.

From the NMR measurement result, it was confirmed that the obtained compound was 4-(diallylethoxysilyl)iodobenzene.

Synthesis Example 3

4-(diallylethoxysilyl)phenol was Prepared as Follows

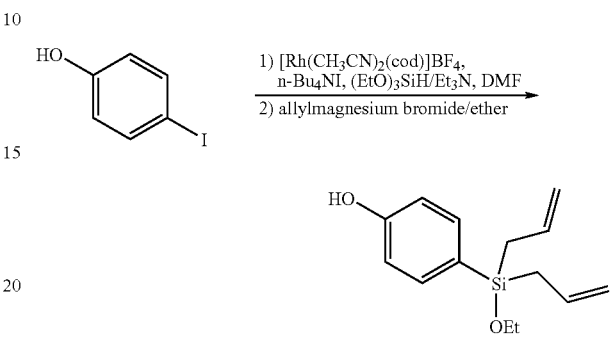

At first, a mixture of 4-iodophenol (6 g, 27.3 mmol) [Rh(CH$_3$CN)$_2$(cod)]BF$_4$(104 mg, 0.27 mmol) and tetrabutylammoniumiodido (n-Bu$_4$NI: 10.0 g, 27.3 mmol) was added dropwise with dist.DMF (180 mL), distilled triethylamine (dist.Et$_3$N: 11.4 mL, 81.8 mmol), and triethoxysilane ((EtO)$_3$SiH: 15.1 mL, 81.8 mmol). Then, the resultant mixture was stirred under a nitrogen atmosphere at 80° C. for 3 hours to obtain a reaction mixture. Subsequently, the solvent in the reaction mixture was distilled with a vacuum pump, and a residue was obtained. Thereafter, the obtained residue was extracted with ether. A salt thus formed was removed by filtering with celite. The solvent was distilled from organic layers with an evaporator to obtain a crude product (I).

After that, the crude product (I) thus obtained was directly added with 1 mol/L of allylmagnesium bromide (136 mL (solvent: ether), 136 mmol) at 0° C. to obtain a mixture product. Then, the mixture product was stirred under a nitrogen atmosphere at room temperature for 19 hours. Subsequently, the obtained mixture product was added with 10% by mass of HCl to terminate the reaction, and 10% by mass of HCl was further added thereto immediately before the point when the salt disappeared. Thereafter, the organic layers were separated from the mixture product, and the aqueous layer was extracted with ether. The collected organic layers were washed with sat.NaHCO$_3$ and sat.NaCl, dried with MgSO$_4$, filtered, and concentrated to obtain a crude product (II). After that, the crude product (II) thus obtained was separated and purified by silica gel column chromatography (hexane/EtOAc=5/1), and thereby 4-(diallylethoxysilyl)phenol was obtained (5.30 g, 78% yield in two steps).

The obtained compound was subjected to $^1$H NMR and $^{13}$C NMR measurements. The obtained results are shown below.
$^1$H NMR (CDCl$_3$) δ 7.46 (d, J=8.6 Hz, 2H), 6.85 (d, J=8.6 Hz, 2H), 5.90-5.74 (m, 2H), 5.57 (br, 1H), 4.99-4.88 (m, 4H), 3.75 (q, J=6.8 Hz, 4H), 1.92 (d, J=8.4 Hz, 4H), 1.20 (t, J=6.8 Hz, 3H).

$^{13}$C NMR (CDCl$_3$) δ 157.2, 135.8, 133.2, 125.9, 115.0, 114.7, 59.3, 21.2, 18.3.

From the NMR measurement results, it was confirmed that the obtained compound was 4-(diallylethoxysilyl)phenol.

Example 3

4-(diallylethoxysilyl)phenyltriflate was Prepared as Follows

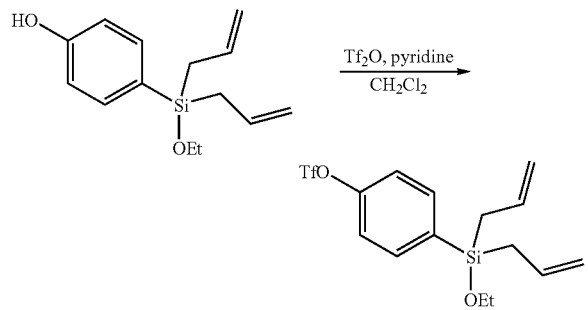

At first, the 4-(diallylethoxysilyl)phenol (102 mg, 0.41 mmol) obtained in Synthesis example 3 was added to distilled dichloromethane (dist.CH$_2$Cl$_2$: 1.9 mL), and dissolved to obtain a solution. Then, the solution was added dropwise with pyridine (133 μL, 1.64 mmol) and trifluoroacetic anhydride (Tf$_2$O: 76 μL, 0.45 mmol) at −78° C. The resultant solution was stirred under a nitrogen atmosphere at room temperature for 25 hours. Subsequently, distilled ethanol (dist.EtOH: 3 mL) was further added, and stirred for 30 minutes to obtain a reaction mixture. Thereafter, the obtained reaction mixture was washed with sat.NaHCO$_3$ and sat.NaCl, dried with MgSO$_4$, filtered, and concentrated to obtain a crude product. After that, the crude product thus obtained was separated and purified by silica gel column chromatography (hexane/EtOAc=5/1), and thereby 4-(diallylethoxysilyl)phenyltriflate was obtained (73.3 mg, 47% yield).

The obtained compound was subjected to $^1$H NMR and $^{13}$C NMR measurements. The obtained results are shown below.
$^1$H NMR (CDCl$_3$) δ 7.67 (d, J=8.1 Hz, 2H), 7.28 (d, J=8.1 Hz, 2H), 5.87-5.71 (m, 2H), 4.99-4.91 (m, 4H), 3.79 (q, J=7.0 Hz, 2H), 1.93 (d, J=7.8 Hz, 4H), 1.23 (t, J=7.0 Hz, 3H).
$^{13}$C NMR (CDCl$_3$) δ 150.9, 136.5, 136.0, 132.4, 132.4, 120.6, 115.2, 59.4, 21.1, 18.3.

From the NMR measurement results, it was confirmed that the obtained compound was 4-(diallylethoxysilyl)phenyltriflate.

Example 4

4-(diallylethoxysilyl)phenyltriflate was Prepared as Follows

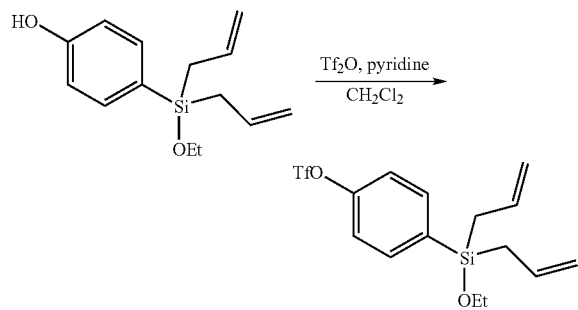

Under a nitrogen atmosphere, a dist.CH$_2$Cl$_2$ solution (10 mL) of pyridine (521 μL, 6.4 mmol) was cooled to −78° C., and further added dropwise with Tf$_2$O (298 μL, 1.76 mmol). The resultant solution was stirred under a nitrogen atmosphere at −78° C. for 15 minutes to obtain a mixed solution. Subsequently, the mixed solution was added dropwise with a dist.CH$_2$Cl$_2$ solution (20 mL) of the 4-(diallylethoxysilyl)phenol (400 mg, 1.61 mmol) obtained in Synthesis example 3 at −78° C. to obtain a reaction mixture. Thereafter the reaction mixture was gradually heated from −78° C. to room temperature, and stirred under a nitrogen atmosphere at room temperature for 19 hours. After that, dist.EtOH (4 mL) was added into the reaction mixture, and further stirred for 30 minutes. Then, the reaction mixture was washed with sat.NaHCO$_3$ and sat.NaCl, dried with MgSO$_4$, filtered, and concentrated to obtain a crude product. Subsequently, the crude product thus obtained was separated and purified by silica gel column chromatography (hexane/EtOAc=10/1), and thereby 4-(diallylethoxysilyl)phenyltriflate was obtained (485 mg, 79% yield).

The obtained compound was subjected to $^1$H NMR and $^{13}$C NMR measurements. The obtained results are shown below.
$^1$H NMR (CDCl$_3$) δ 7.67 (d, J=8.1 Hz, 2H), 7.28 (d, J=8.1 Hz, 2H), 5.87-5.71 (m, 2H), 4.99-4.91 (m, 4H), 3.79 (q, J=7.0 Hz, 2H), 1.93 (d, J=7.8 Hz, 4H), 1.23 (t, J=7.0 Hz, 3H).
$^{13}$C NMR (CDCl$_3$) δ 150.9, 136.5, 136.0, 132.4, 132.4, 120.6, 115.2, 59.4, 21.1, 18.3.

From the NMR measurement results, it was confirmed that the obtained compound was 4-(diallylethoxysilyl)phenyltriflate.

Example 5

4-(diallylethoxysilyl)phenyltriflate was Prepared as Follows

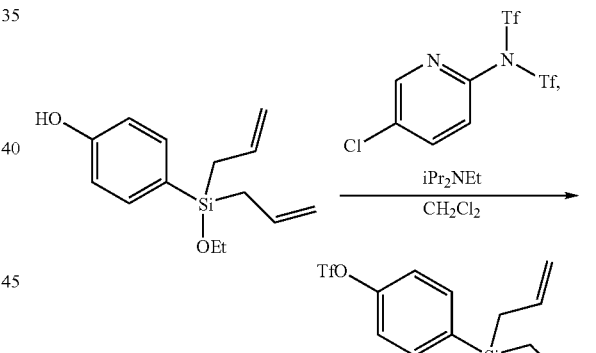

At first, a mixture of the 4-(diallylethoxysilyl)phenol (197 mg, 0.79 mmol) obtained in Synthesis example 3 and 2-[N,N-bis(trifluoromethylsulfonyl)amino]-5-chloropyridine (343 mg, 0.87 mmol) was added with dist.CH$_2$Cl$_2$ (5 mL), and dissolved to obtain a solution. Then, the solution was added dropwise with N,N-diisopropylethylamine (iPr$_2$NEt: 553 μL, 3.17 mmol) at room temperature. Subsequently, the resultant solution was stirred under a nitrogen atmosphere at room temperature for 19 hours to obtain a reaction mixture. Thereafter, the organic layer in the obtained reaction mixture was concentrated to obtain a crude product. The crude product thus obtained was separated and purified by silica gel column chromatography (hexane/EtOAc=10/1), and thereby 4-(diallylethoxysilyl)phenyltriflate was obtained (253 mg, 84% yield).

The obtained compound was subjected to $^1$H NMR and $^{13}$C NMR measurements. The obtained results are shown below.

$^1$H NMR (CDCl$_3$) δ 7.67 (d, J=8.1 Hz, 2H), 7.28 (d, J=8.1 Hz, 2H), 5.87-5.71 (m, 2H), 4.99-4.91 (m, 4H), 3.79 (q, J=7.0 Hz, 2H), 1.93 (d, J=7.8 Hz, 4H), 1.23 (t, J=7.0 Hz, 3H).
$^{13}$C NMR (CDCl$_3$) δ 150.9, 136.5, 136.0, 132.4, 132.4, 120.6, 115.2, 59.4, 21.1, 18.3.

From the NMR measurement results, it was confirmed that the obtained compound was 4-(diallylethoxysilyl)phenyltriflate.

Example 6

1-(diallylethoxysilyl)-4-(4,4,5,5-tetramethyl-1,3,2-dioxaborolan-2-yl)benzene was Prepared as Follows

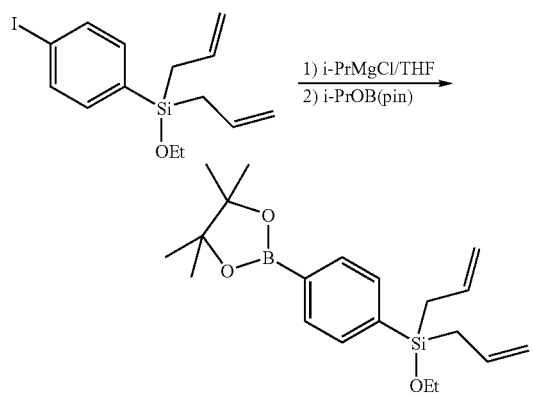

A THF solution (2 mL) of the 4-(diallylethoxysilyl)iodobenzene (171 mg, 0.48 mmol) obtained in Example 2 was added dropwise with 2 mol/L of i-PrMgCl (0.50 mL (solvent: THF), 1.0 mmol) at −30° C. Then, the resultant solution was stirred under a nitrogen atmosphere at −30° C. for 1.5 hours to obtain a THF solution containing 4-(diallylethoxysilyl)phenylmagnesium chloride (Grignrad solution). Subsequently, the obtained Grignrad solution was cooled to −78° C., and added dropwise with 2-isopropoxy-4,4,5,5-tetramethyl-1,3,2-dioxaborolane (204 μL, 1.0 mmol) to obtain a reaction mixture. Thereafter, the obtained reaction mixture was stirred under a nitrogen atmosphere at −78° C. for one hour, and further stirred at room temperature for 14 hours. After that, the reaction mixture was added with distilled water to terminate the reaction, and 10% by mass of an HCl solution was further added thereto until the salt thus formed disappeared. Then, the organic layer was separated therefrom, and the aqueous layer was extracted with ether to collect the organic layer. Subsequently, the organic layer thus collected was washed with sat.NaHCO$_3$ and sat.NaCl, dried with MgSO$_4$, filtered, and concentrated to obtain a crude product. Thereafter, the crude product thus obtained was separated and purified by silica gel column chromatography (hexane/EtOAc=5/1), and thereby 1-(diallylethoxysilyl)-4-(4,4,5,5-tetramethyl-1,3,2-di oxaborolan-2-yl)benzene was obtained (128.3 mg, 75% yield).

The obtained compound was subjected to $^1$H NMR and $^{13}$C NMR measurements. The obtained results are shown below.
$^1$H NMR (CDCl$_3$) δ 7.81 (d, J=8.4 Hz, 2H), 7.58 (d, J=8.4 Hz, 2H), 5.89-5.73 (m, 2H), 4.98-4.87 (m, 4H), 3.75 (q, J=7.0 Hz, 2H), 1.94 (d, J=7.8 Hz, 4H), 1.34 (s, 12H), 1.20 (t, J=7.0 Hz, 3H). $^{13}$C NMR (CDCl$_3$) δ 138.5, 133.8, 133.2, 132.9, 127.7, 114.8, 83.8, 59.3, 24.8, 21.1, 18.3.

From the NMR measurement results, it was confirmed that the obtained compound was 1-(diallylethoxysilyl)-4-(4,4,5,5-tetramethyl-1,3,2-di oxaborolan-2-yl)benzene.

Example 7

4-(diallylethoxysilyl)phenyl-trimethyltin was Prepared as Follows

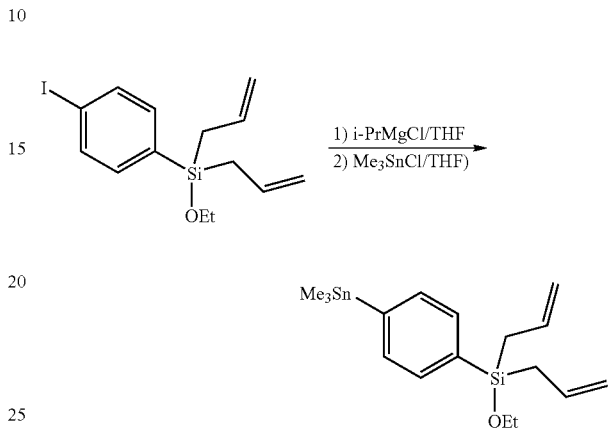

At first, a THF solution (2 mL) of the 4-(diallylethoxysilyl) iodobenzene (202 mg, 0.56 mmol) obtained in Example 2 was added dropwise with 2 mol/L of i-PrMgCl (0.59 mL (solvent: THF), 1.18 mmol) at −30° C. Then, the resultant solution was stirred under a nitrogen atmosphere at −30° C. for 1.5 hours to obtain a THF solution containing 4-(diallylethoxysilyl)phenylmagnesium chloride (Grignrad solution). Subsequently, the obtained Grignrad solution was added dropwise with 1 mol/L of trimethyl tin chloride (Me$_3$SnCl: 1.18 mL (solvent: THF), 1.18 mmol) at −30° C. to obtain a reaction mixture. Thereafter, the reaction mixture was stirred under a nitrogen atmosphere at room temperature for 13 hours, and added with distilled water to terminate the reaction. After that, the organic layer was separated from the reaction mixture, and the aqueous layer was extracted with ether to collect the organic layer. Subsequently, the organic layer thus collected was washed with sat.NaHCO$_3$ and sat.NaCl, dried with MgSO$_4$, filtered, and concentrated to obtain a crude product. Thereafter, the crude product thus obtained was separated and purified by silica gel column chromatography (hexane/EtOAc=5/1), and thereby 4-(diallylethoxysilyl)phenyl-trimethyltin was obtained (214 mg, 96% yield).

The obtained compound was subjected to $^1$H NMR and $^{13}$C NMR measurements. The obtained results are shown below.
$^1$H NMR (CDCl$_3$) δ 7.52 (d, J=1.62 Hz, 4H), 5.89-5.79 (m, 2H), 5.00-4.89 (m, 4H), 3.76 (q, J=6.8 Hz, 2H), 1.93 (d, J=8.1 Hz, 4H), 1.21 (t, J=6.8 Hz, 3H), 0.29 (s, 9H, J (Sn—CH$_3$=54.5 Hz)).
$^{13}$C NMR (CDCl$_3$) δ 144.6, 135.3, 134.8, 133.4, 133.2, 114.7, 59.3, 21.2, 18.4-9.63 (J($^{119}$Sn—CH$_3$)=348.6 Hz, J($^{117}$Sn—CH$_3$)=333.0 Hz).

From the NMR measurement results, it was confirmed that the obtained compound was 4-(diallylethoxysilyl)phenyl-trimethyltin.

Example 8

4-(diallylethoxysilyl)biphenyl was Prepared as Follows

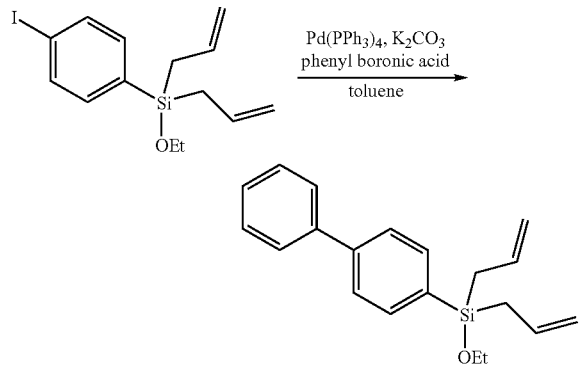

At first, a mixture of the 4-(diallylethoxysilyl)iodobenzene (148 mg, 0.41 mmol) obtained in Example 2, tetrakistriphenylphosphine palladium (Pd(PPh$_3$)$_4$: 14.3 mg, 0.012 mmol), potassium carbonate (K$_2$CO$_3$: 85.1 mg, 0.62 mmol), and phenyl boronic acid (60 mg, 0.49 mmol) was added with distilled toluene (dist.toluene: 5 mL). Subsequently, the resultant mixture was stirred under a nitrogen atmosphere at 80° C. for 13 hours to obtain a reaction mixture. Thereafter, the reaction mixture was diluted with ether, and a salt thus formed was removed by filtering with celite. The solvent was distilled from the organic layer with an evaporator to obtain a crude product. After that, the crude product thus obtained was separated and purified by silica gel column chromatography (hexane/EtOAc=10/1), and thereby 4-(diallylethoxysilyl)biphenyl (a second organosilane compound of the present invention) was obtained (99.6 mg, 78% yield).

The obtained compound was subjected to $^1$H NMR and $^{13}$C NMR measurements. The obtained results are shown below.
$^1$H NMR (CDCl$_3$) δ 7.68-7.60 (m, 6H), 7.45 (t, J=7.0 Hz, 2H), 7.36 (t, J=7.0 Hz, 1H), 5.94-5.78 (m, 2H), 5.02-4.91 (m, 4H), 3.80 (q, J=6.8 Hz, 2H), 1.97 (d, J=7.8 Hz, 2H), 1.23 (t, J=6.8 Hz, 3H).
$^{13}$C NMR (CDCl$_3$) δ 142.4, 140.8, 134.5, 133.7, 133.1, 128.7, 127.4, 127.1, 126.4, 114.8, 59.3, 21.2, 18.4.

From the NMR measurement results, it was confirmed that the obtained compound was 4-(diallylethoxysilyl)biphenyl having a phenyl group as Ar' in the general formula (2).

Example 9

4-(diallylethoxysilyl)biphenyl was Prepared as Follows

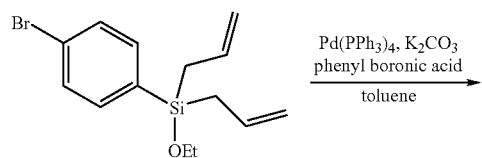 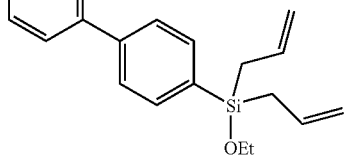

-continued

A mixture of the 4-(diallylethoxysilyl)bromobenzene (152 mg, 0.49 mmol) obtained in Example 1, Pd(PPh$_3$)$_4$ (16.9 mg, 0.015 mmol), K$_2$CO$_3$ (101 mg, 0.73 mmol), and phenyl boronic acid (71.4 mg, 0.59 mmol) was added with dist.toluene (5 mL). Subsequently, the resultant mixture was stirred under a nitrogen atmosphere at 80° C. for 13 hours to obtain a reaction mixture. Thereafter, a salt formed in the reaction mixture was removed by filtering with celite. The solvent was distilled from the organic layer with an evaporator to obtain a crude product. After that, the crude product thus obtained was separated and purified by silica gel column chromatography (hexane/EtOAc=10/1), and thereby 4-(diallylethoxysilyl)biphenyl was obtained (91.2 mg, 61% yield).

The obtained compound was subjected to $^1$H NMR and $^{13}$C NMR measurements. The obtained results are shown below.
$^1$H NMR (CDCl$_3$) δ 7.68-7.60 (m, 6H), 7.45 (t, J=7.0 Hz, 2H), 7.36 (t, J=7.0 Hz, 1H), 5.94-5.78 (m, 2H), 5.02-4.91 (m, 4H), 3.80 (q, J=6.8 Hz, 2H), 1.97 (d, J=7.8 Hz, 2H), 1.23 (t, J=6.8 Hz, 3H).
$^{13}$C NMR (CDCl$_3$) δ 142.4, 140.8, 134.5, 133.7, 133.1, 128.7, 127.4, 127.1, 126.4, 114.8, 59.3, 21.2, 18.4.

From the NMR measurement results, it was confirmed that the obtained compound was 4-(diallylethoxysilyl)biphenyl having a phenyl group as Ar' in the general formula (2).

Example 10

4-(diallylethoxysilyl)-4'-methoxybiphenyl was Prepared as Follows

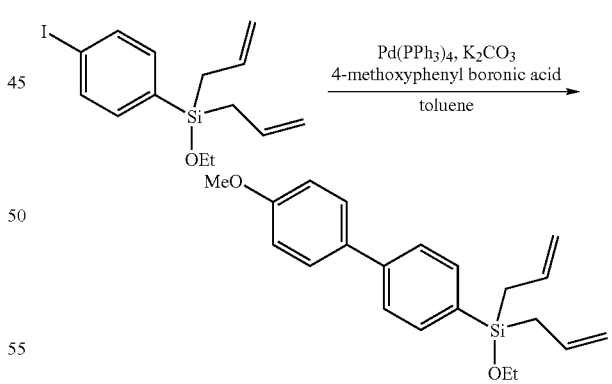

At first, a mixture of the 4-(diallylethoxysilyl)iodobenzene (187 mg, 0.52 mmol) obtained in Example 2, Pd(PPh$_3$)$_4$ (18.1 mg, 0.016 mmol), K$_2$CO$_3$ (108 mg, 0.78 mmol), and 4-methoxyphenyl boronic acid (95.2 mg, 0.63 mmol) was added with dist.toluene (5 mL). Subsequently, the resultant mixture was stirred under a nitrogen atmosphere at 80° C. for 13 hours to obtain a reaction mixture. Thereafter, a salt formed in the reaction mixture was removed by filtering with celite. The solvent was distilled from the organic layer with an evaporator to obtain a crude product. After that, the crude product thus obtained was separated and purified by silica gel column chromatography (hexane/EtOAc=10/1), and thereby 4-(diallylethoxysilyl)-4'-methoxybiphenyl was obtained (157.3 mg, 89% yield).

The obtained compound was subjected to $^1$H NMR and $^{13}$C NMR measurements. The obtained results are shown below.
$^1$H NMR (CDCl$_3$) δ 7.63 (d, J=7.6 Hz, 2H), 7.57 (d, J=7.6 Hz, 2H), 7.55 (d, J=8.4 Hz, 2H), 6.99 (d, J=8.4 Hz, 2H), 5.94-5.78 (m, 2H), 5.02-4.91 (m, 4H), 3.86 (s, 3H), 3.79 (q, J=6.8 Hz, 2H), 1.97 (d, J=8.1 Hz, 2H), 1.23 (t, J=6.8 Hz, 3H).

$^{13}$C NMR (CDCl$_3$) δ 159.3, 142.0, 134.4, 133.3, 133.1, 132.9, 128.1, 126.0, 114.7, 114.2, 59.3, 55.2, 21.2, 18.4. From the NMR measurement results, it was confirmed that the obtained compound was 4-(diallylethoxysilyl)-4'-methoxybiphenyl having a methoxyphenyl group as Ar' in the general formula (2).

Example 11

4-(diallylethoxysilyl)-4'-methoxybiphenyl was Prepared as Follows

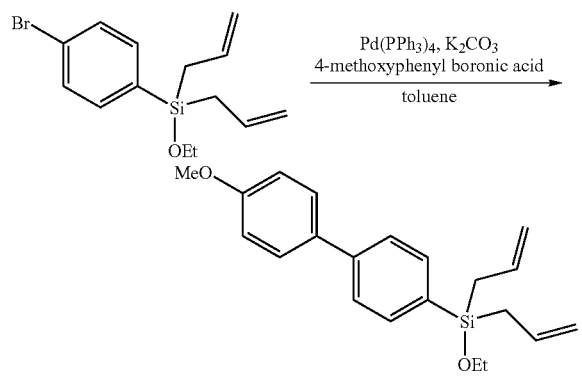

At first, a mixture of the 4-(diallylethoxysilyl)bromobenzene (191 mg, 0.61 mmol) obtained in Example 1, Pd(PPh$_3$)$_4$ (21.3 mg, 0.018 mmol), K$_2$CO$_3$ (127 mg, 0.92 mmol), and 4-methoxyphenyl boronic acid (112 mg, 0.74 mmol) was added with dist.toluene (5 mL). Subsequently, the resultant mixture was stirred under a nitrogen atmosphere at 80° C. for 13 hours to obtain a reaction mixture. Thereafter, a salt formed in the reaction mixture was removed by filtering with celite. The solvent was distilled from the organic layer with an evaporator to obtain a crude product. After that, the crude product thus obtained was separated and purified with PTLC (hexane/EtOAc=10/1), and thereby 4-(diallylethoxysilyl)-4'-methoxybiphenyl was obtained (125.4 mg, 60% yield).

The obtained compound was subjected to $^1$H NMR and $^{13}$C NMR measurements. The obtained results are shown below.
$^1$H NMR (CDCl$_3$) δ 7.63 (d, J=7.6 Hz, 2H), 7.57 (d, J=7.6 Hz, 2H), 7.55 (d, J=8.4 Hz, 2H), 6.99 (d, J=8.4 Hz, 2H), 5.94-5.78 (m, 2H), 5.02-4.91 (m, 4H), 3.86 (s, 3H), 3.79 (q, J=6.8 Hz, 2H), 1.97 (d, J=8.1 Hz, 2H), 1.23 (t, J=6.8 Hz, 3H).

$^{13}$C NMR (CDCl$_3$) δ 159.3, 142.0, 134.4, 133.3, 133.1, 132.9, 128.1, 126.0, 114.7, 114.2, 59.3, 55.2, 21.2, 18.4. From the NMR measurement results, it was confirmed that the obtained compound was 4-(diallylethoxysilyl)-4'-methoxybiphenyl having a methoxyphenyl group as Ar' in the general formula (2).

Example 12

4-(diallylethoxysilyl)-4'-methoxybiphenyl was Prepared as Follows

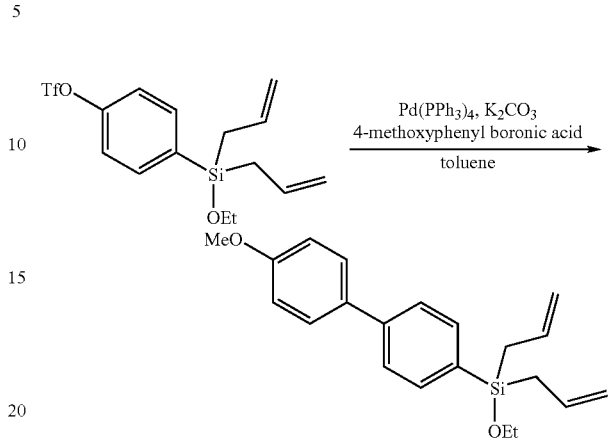

At first, a mixture of the 4-(diallylethoxysilyl)phenyltriflate (150 mg, 0.39 mmol) obtained in Example 4, Pd(PPh$_3$)$_4$ (13.6 mg, 0.012 mmol), K$_2$CO$_3$ (81.7 mg, 0.59 mmol), and 4-methoxyphenyl boronic acid (71.9 mg, 0.47 mmol) was added with dist.toluene (5 mL). Subsequently, the resultant mixture was stirred under a nitrogen atmosphere at 80° C. for 16 hours to obtain a reaction mixture. Thereafter, a salt formed in the reaction mixture was removed by filtering with celite. The solvent was distilled from the organic layer with an evaporator to obtain a crude product. After that, the obtained crude product was separated and purified by silica gel column chromatography (hexane/EtOAc=10/1), and thereby 4-(diallylethoxy-silyl)-4'-methoxybiphenyl was obtained (101.7 mg, 76% yield).

The obtained compound was subjected to $^1$H NMR and $^{13}$C NMR measurements. The obtained results are shown below.
$^1$H NMR (CDCl$_3$) δ 7.63 (d, J=7.6 Hz, 2H), 7.57 (d, J=7.6 Hz, 2H), 7.55 (d, J=8.4 Hz, 2H), 6.99 (d, J=8.4 Hz, 2H), 5.94-5.78 (m, 2H), 5.02-4.91 (m, 4H), 3.86 (s, 3H), 3.79 (q, J=6.8 Hz, 2H), 1.97 (d, J=8.1 Hz, 2H), 1.23 (t, J=6.8 Hz, 3H).

$^{13}$C NMR (CDCl$_3$) δ 159.3, 142.0, 134.4, 133.3, 133.1, 132.9, 128.1, 126.0, 114.7, 114.2, 59.3, 55.2, 21.2, 18.4. From the NMR measurement results, it was confirmed that the obtained compound was 4-(diallylethoxysilyl)-4'-methoxybiphenyl having a methoxyphenyl group as Ar' in the general formula (2).

Example 13

An Organosilica was Synthesized as Follows

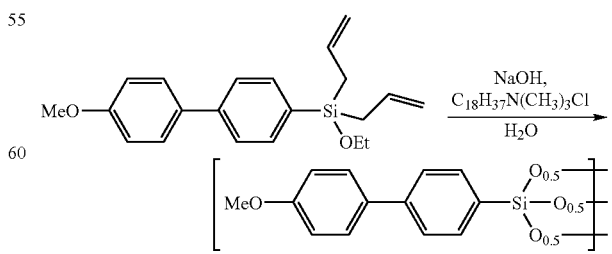

At first, a mixture of trimethylstearylammonium chloride (20 mg), water (1.1 g), and 6 mol/L of a sodium hydroxide aqueous solution (20 μL) was added with the 4-diallylethoxysilyl-4'-methoxybiphenyl (25 mg) obtained in Example 12. Subsequently, the resultant mixture was vigorously stirred at room temperature (25° C.) overnight (24 hours). After the stirring was ceased, the suspension thus obtained was heated at 90° C. for 24 hours. Thereafter, a whitish precipitate formed in the suspension was recovered by suction filtration, washed with water, and then dried under a reduced pressure. Thereby, an organosilica having a methoxybiphenyl group was obtained (whitish powder yield: 19.6 mg).

Figure 4:
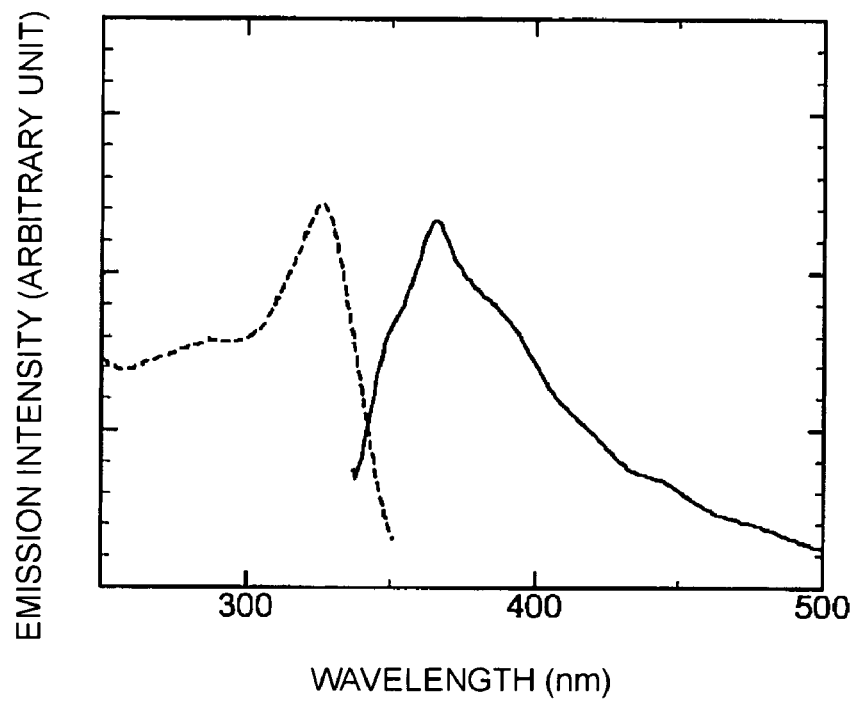
FIG. 4 is a graph showing an excitation spectrum (dashed line) and a fluorescence spectrum (solid line) of an organosilica obtained in Example 13.

The obtained organosilica powder was subjected to excitation and fluorescence spectrum measurements. FIG. 4 shows a graph of the excitation spectrum (dashed line) and the fluorescence spectrum (solid line) thus obtained. As apparent from the result shown in FIG. 4, it was observed that the obtained organosilica powder absorbed light at 327 nm and emitted fluorescence at 365 nm.

From the result, it was found that the obtained organosilica is preferably used as an optical functional material. It was also found that, when the second organosilane compound (Example 12) of the present invention is used, it is possible to efficiently synthesize, under a basic condition at a relatively moderate heating temperature, an organosilica having a light absorbing function and a fluorescence function.

Example 14

An Organosilica was Synthesized as Follows

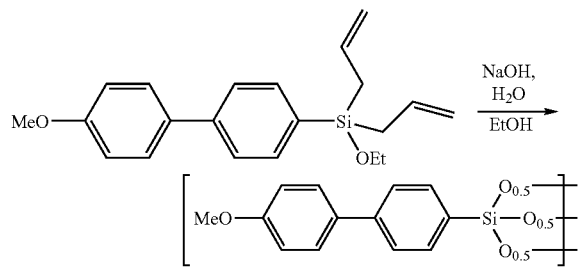

At first, the 4-diallylethoxysilyl-4'-methoxybiphenyl (25 mg) obtained in Example 12 was dissolved in ethanol (1.0 g), and then added with water (0.1 g) and 6 mol/L of a sodium hydroxide aqueous solution (20 μL). Subsequently, the resultant mixture was stirred at room temperature (25° C.) overnight (24 hours). After the stirring was ceased, the obtained reaction solution was heated at 70° C. for 24 hours. Thereafter, a whitish precipitate formed in the reaction solution was recovered by suction filtration, washed with ethanol, and then dried under a reduced pressure. Thereby, an organosilica having a methoxybiphenyl group was obtained (whitish powder yield: 14.7 mg).

Figure 5:
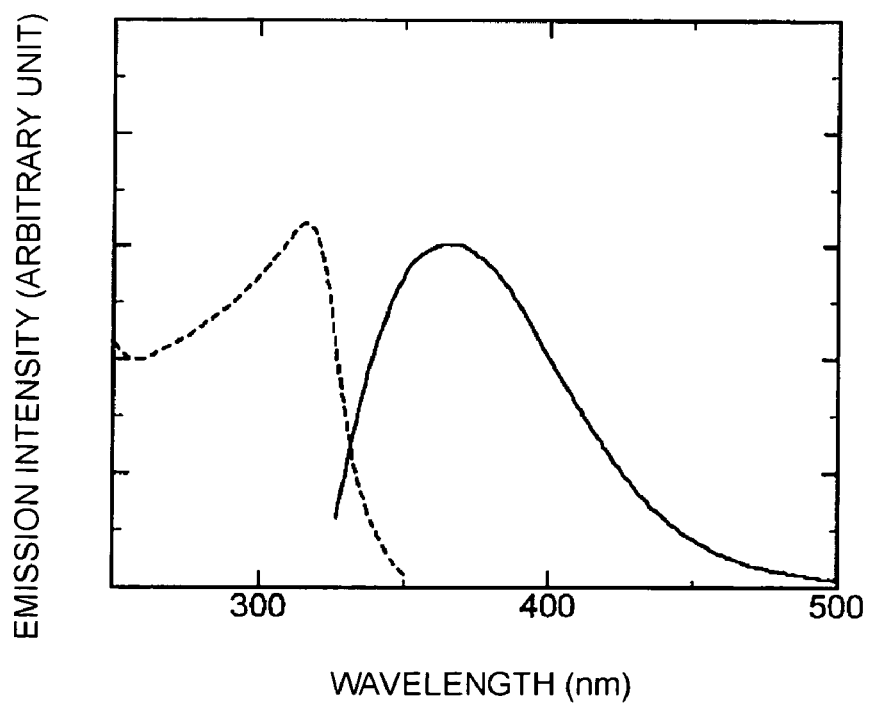
FIG. 5 is a graph showing an excitation spectrum (dashed line) and a fluorescence spectrum (solid line) of an organosilica obtained in Example 14.

The obtained organosilica powder was subjected to excitation and fluorescence spectrum measurements. FIG. 5 shows a graph of the excitation spectrum (dashed line) and the fluorescence spectrum (solid line) thus obtained. As apparent from the result shown in FIG. 5, it was observed that the obtained organosilica powder absorbed light at 316 nm and emitted fluorescence at 366 nm.

From the result, it was found that the obtained organosilica is preferably used as an optical functional material. It was also found that, when the second organosilane compound (Example 12) of the present invention is used, it is possible to efficiently synthesize, under a basic condition at relatively moderate stirring and heating temperatures, an organosilica having a light absorbing function and a light emitting function.

Example 15

An Organosilica was Synthesized as Follows

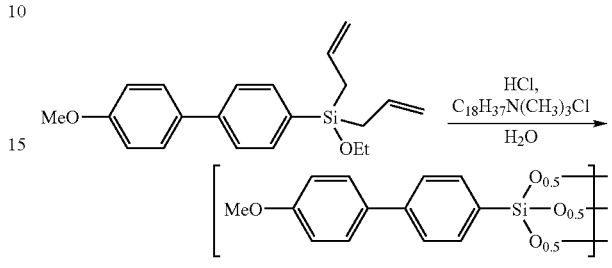

At first, a mixture of trimethylstearylammonium chloride (25 mg), water (1.0 g), and 2 mol/L of hydrochloric acid (1.0 g) was added with the 4-diallylethoxysilyl-4'-methoxybiphenyl (25 mg) obtained in Example 12. Subsequently, the resultant mixture was vigorously stirred at room temperature (25° C.) overnight (24 hours). After the stirring was ceased, the suspension thus obtained was heated at 90° C. for 24 hours. Thereafter, a whitish precipitate formed in the suspension was recovered by suction filtration, washed with water, and then dried under a reduced pressure. Thereby, an organosilica having a methoxybiphenyl group was obtained (whitish powder yield: 14.0 mg).

Figure 6:
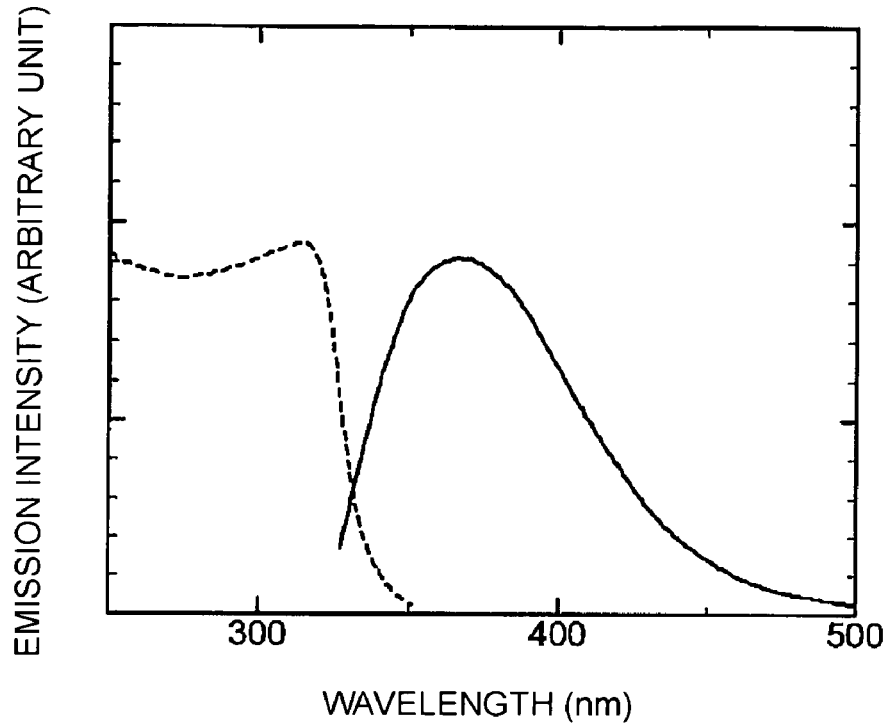
FIG. 6 is a graph showing an excitation spectrum (dashed line) and a fluorescence spectrum (solid line) of an organosilica obtained in Example 15.

The obtained organosilica powder was subjected to excitation and fluorescence spectrum measurements. FIG. 6 shows a graph of the excitation spectrum (dashed line) and the fluorescence spectrum (solid line) thus obtained. As apparent from the result shown in FIG. 6, it was observed that the obtained organosilica powder absorbed light at 314 nm and emitted fluorescence at 367 nm.

From the result, it was found that the obtained organosilica is preferably used as an optical functional material. It was also found that, when the second organosilane compound (Example 12) of the present invention is used, it is possible to efficiently synthesize, under an acidic condition at a relatively moderate heating temperature, an organosilica having a light-absorbing function and a light emitting function.

Example 16

An Organosilica was Synthesized as Follows

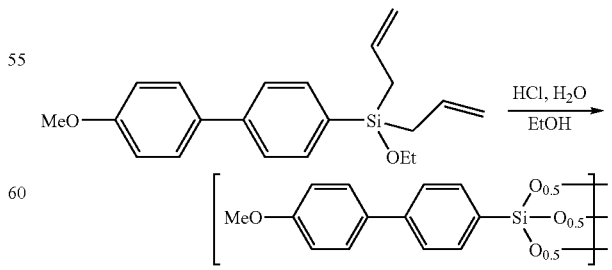

At first, the 4-diallylethoxysilyl-4'-methoxybiphenyl (25 mg) obtained in Example 12 was dissolved in ethanol (2.0 g), and then added with 2 mol/L of hydrochloric acid (0.7 g).

Subsequently, the resultant mixture was stirred at room temperature (25° C.) overnight (24 hours). After the stirring was ceased, the obtained reaction solution was heated at 70° C. for 24 hours. Thereafter, a whitish precipitate formed in the reaction solution was recovered by suction filtration, washed with ethanol, and then dried under a reduced pressure. Thereby, an organosilica having a methoxybiphenyl group was obtained (whitish powder yield: 10.5 mg).

Figure 7:
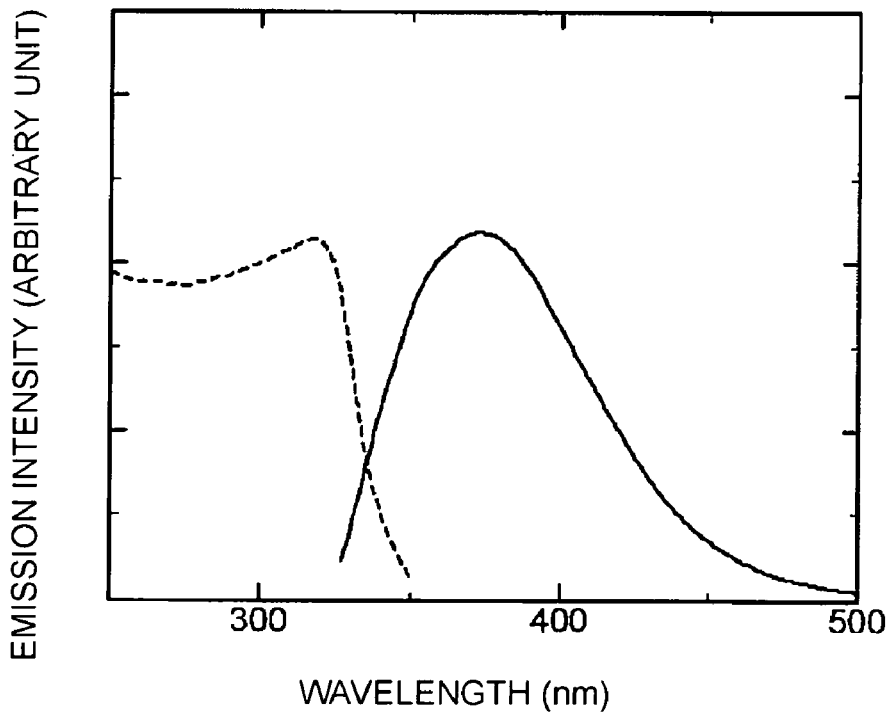
FIG. 7 is a graph showing an excitation spectrum (dashed line) and a fluorescence spectrum (solid line) of an organosilica obtained in Example 16.

The obtained organosilica powder was subjected to excitation and fluorescence spectrum measurements. FIG. 7 shows a graph of the excitation spectrum (dashed line) and the fluorescence spectrum (solid line) thus obtained. As apparent from the result shown in FIG. 7, it was observed that the obtained organosilica powder absorbed light at 318 nm and emitted fluorescence at 374 nm.

From the result, it was found that the obtained organosilica is preferably used as an optical functional material. It was also found that, when the second organosilane compound (Example 12) of the present invention is used, it is possible to efficiently synthesize, under an acidic condition at relatively moderate stirring and heating temperatures, an organosilica having a light-absorbing function and a light emitting function.

Example 17

4-(diallylhydroxysilyl)iodobenzene was Prepared as Follows

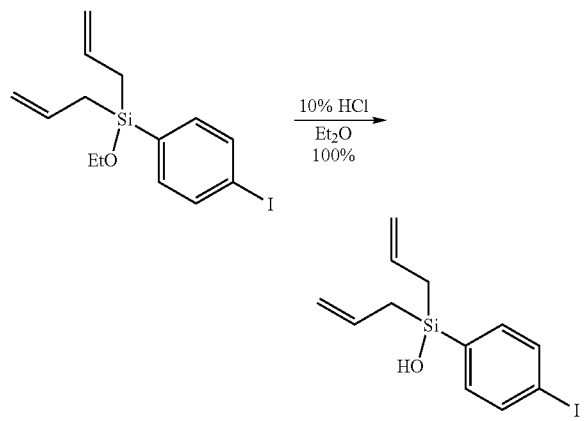

4-(diallylethoxysilyl)iodobenzene (1.19 g, 3.32 mmol) was dissolved in diethyl ether (Et$_2$O: 20 mL), and thoroughly stirred while being added with 10% by mass of an HCl solution until the pH of the mixed solution reached approximately 3 to obtain a reaction solution. Subsequently, the hydrolysis reaction in the reaction solution thus obtained was traced with TLC. When the reaction was ceased, the organic layer was washed with sat.NaHCO$_3$ and sat.NaCl, dried with MgSO$_4$, filtered, and concentrated to obtain a crude product. Thereafter, the crude product thus obtained was separated and purified by silica gel column chromatography (hexane/EtOAc=3/1), and thereby 4-(diallylethoxysilyl)iodobenzene was obtained (1.09 g, 100% yield).

The obtained compound was subjected to a $^1$H NMR measurement. The obtained result is shown below.

$^1$H NMR (CDCl$_3$) δ 1.89 (d, J=7.8 Hz, 4H), 2.19 (s, 1H), 4.92-4.99 (m, 4H), 5.78 (ddt, J=16.2 Hz, 10.3 Hz, 7.8 Hz, 2H), 7.30 (d, J=8.1 Hz, 2H), 7.73 (d, J=8.1 Hz, 2H).

From the NMR measurement result, it was confirmed that the obtained compound was 4-(diallylhydroxysilyl)iodobenzene.

Example 18

4-(diallylhydroxysilyl)-4'-methoxybiphenyl was Prepared as Follows. (Suzuki Coupling Reaction with a silanol-iodo Compound)

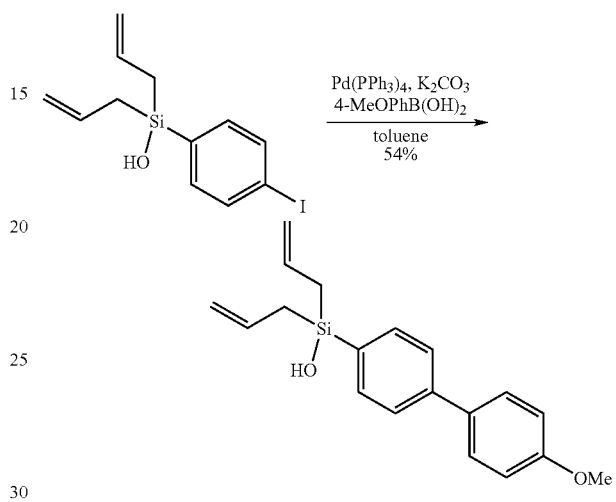

A mixture of the 4-(diallylhydroxysilyl)iodobenzene (151 mg, 0.46 mmol) obtained in Example 17, Pd(PPh$_3$)$_4$ (15.9 mg, 0.014 mmol), K$_2$CO$_3$ (94.8 mg, 0.69 mmol), and 4-methoxyphenyl boronic acid (83.4 mg, 0.55 mmol) was added with dist.toluene (5 mL). Subsequently, the resultant mixture was stirred under a nitrogen atmosphere at 80° C. for 38 hours to obtain a reaction mixture. Thereafter, a salt formed in the reaction mixture was removed by filtering with celite. The solvent was distilled from the organic layer with an evaporator to obtain a crude product. After that, the crude product thus obtained was separated and purified by silica gel column chromatography (hexane/EtOAc=3/1), and thereby 4-(diallylhydroxysilyl)-4'-methoxybiphenyl was obtained (76.1 mg, 54% yield).

The obtained compound was subjected to a $^1$H NMR measurement. The obtained result is shown below.

$^1$H NMR (CDCl$_3$) δ 1.97 (d, J=8.1 Hz, 4H), 2.18 (s, 1H), 3.85 (s, 3H), 4.95 (dd, J=9.5 Hz, 1.6 Hz, 2H), 5.00 (dd, J=16.5 Hz, 1.6 Hz, 2H), 5.85 (ddt, J=16.5 Hz, 9.5 Hz, 8.1 Hz, 2H), 6.98 (d, J=8.9 Hz, 2H), 7.55 (d, J=8.9 Hz, 2H), 7.57 (d, J=8.1 Hz, 2H), 7.64 (d, J=8.1 Hz, 2H).

From the NMR measurement result, it was confirmed that the obtained compound was 4-(diallylhydroxysilyl)-4'-methoxybiphenyl.

As has been described, the present invention makes it possible to provide an organosilane compound having a sufficiently high chemical stability, and being useful for a synthesis of a mesostructured organosilica as well as a synthesis of an organosilica having a function, such as a refractive index controlling function, a light absorbing function, a light emitting function, and a charge transferring function. The present invention also makes it possible to provide an organosilica obtained from the organosilane compound.

Therefore, the organosilane compound of the present invention is particularly useful as a production material for an organosilica which has a function, such as a refractive index controlling function, a light absorbing function, a light emitting function, and a charge transferring function.

What is claimed is:

1. An organosilane compound, expressed by the following general formula (1):

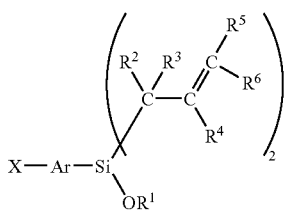

wherein:
- Ar represents any one divalent aromatic organic group selected from the group consisting of a phenylene group, a biphenylylene group, a naphthylene group and a pyridylene group;
- $R^1$ represents any one of a hydrogen atom and alkyl groups having 1 to 4 carbon atoms;
- $R^2$ to $R^6$, which may be the same or different from each other, each represents any one substituent selected from the group consisting of a hydrogen atom, a methyl group, an ethyl group, a propyl group, a butyl group, an isopropyl group, a pentyl group, a hexyl group, and a cyclohexyl group; and
- X represents any one reactive substituent selected from the group consisting of a halogen atom, a magnesium halide, a zinc halide, a stannyl group which may have a substituent, a boranyl group which may have a substituent, and a triflate group.

2. The organosilane compound according to claim 1, wherein Ar in the general formula (1) is the phenylene group.

3. The organosilane compound according to claim 1, wherein $R^1$ in the general formula (1) is any one selected from the group consisting of a methyl group and an ethyl group.

4. The organosilane compound according to claim 1, wherein X in the general formula (1) is any one selected from the group consisting of the halogen atom, the boranyl group, and the triflate group.

5. An organosilica, comprising a polymer of at least one organosilane expressed by general formula (1):

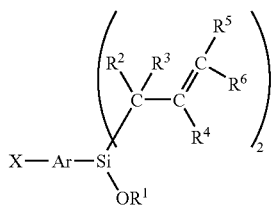

wherein:
- Ar represents any one divalent aromatic organic group selected from the group consisting of a phenylene group, a biphenylylene group, a naphthylene group and a pyridylene group;
- $R^1$ represents any one of a hydrogen atom and alkyl groups having 1 to 4 carbon atoms;
- $R^2$ to $R^6$, which may be the same or different from each other, each represents any one substituent selected from the group consisting of a hydrogen atom, a methyl group, an ethyl group, a propyl group, a butyl group, an isopropyl group, a pentyl group, a hexyl group, and a cyclohexyl group; and
- X represents any one reactive substituent selected from the group consisting of a halogen atom, a magnesium halide, a zinc halide, a stannyl group which may have a substituent, a boranyl group which may have a substituent, and a triflate group.

* * * * *